(12) United States Patent
Sugawara et al.

(10) Patent No.: US 11,129,527 B2
(45) Date of Patent: Sep. 28, 2021

(54) VISUAL FIELD/VISUAL ACUITY EXAMINATION SYSTEM, VISUAL FIELD/VISUAL ACUITY EXAMINATION DEVICE, VISUAL FIELD/VISUAL ACUITY EXAMINATION METHOD, VISUAL FIELD/VISUAL ACUITY EXAMINATION PROGRAM, AND SERVER DEVICE

(71) Applicant: QD Laser, Inc., Kanagawa (JP)

(72) Inventors: Mitsuru Sugawara, Kanagawa (JP); Makoto Suzuki, Kanagawa (JP); Kinya Hasegawa, Kanagawa (JP)

(73) Assignee: QD Laser, Inc., Kanagawa (JP)

( * ) Notice: Subject to any disclaimer, the term of this patent is extended or adjusted under 35 U.S.C. 154(b) by 154 days.

(21) Appl. No.: 16/306,694

(22) PCT Filed: Jun. 7, 2017

(86) PCT No.: PCT/JP2017/021211
§ 371 (c)(1),
(2) Date: Dec. 3, 2018

(87) PCT Pub. No.: WO2017/213200
PCT Pub. Date: Dec. 14, 2017

(65) Prior Publication Data
US 2019/0133437 A1    May 9, 2019

(30) Foreign Application Priority Data

Jun. 9, 2016 (JP) .............................. JP2016-115045
May 30, 2017 (JP) .............................. JP2017-106337

(51) Int. Cl.
*A61B 3/032* (2006.01)
*A61B 3/00* (2006.01)
(Continued)

(52) U.S. Cl.
CPC ............ *A61B 3/032* (2013.01); *A61B 3/0008* (2013.01); *A61B 3/0033* (2013.01);
(Continued)

(58) Field of Classification Search
CPC .. A61B 3/024; A61B 3/028; G02B 2027/0178
(Continued)

(56) References Cited

U.S. PATENT DOCUMENTS 4,971,434 A    11/1990 Ball
5,121,981 A    6/1992 Waltuck et al.
(Continued)

FOREIGN PATENT DOCUMENTS

JP    2002-531152    9/2002
JP    2003-000542    1/2003
(Continued)

OTHER PUBLICATIONS

Extended European search report for European Patent Application No. 17810374.3 dated May 23, 2019.
(Continued)

*Primary Examiner* — Zachary W Wilkes
(74) *Attorney, Agent, or Firm* — IPUSA, PLLC

(57) ABSTRACT

A visual field/visual acuity examination system includes a retinal projection head-mounted display; and a terminal device. The terminal device outputs examination image data to the retinal projection head-mounted display; displays an image on a display; and generates an examination image based on the examination image data and display the examination image on the display. The retinal projection head-mounted display inputs the examination image data from the terminal device; generates an image light beam based on the input examination image data and control emission of the image light beam from a light source; causes a scanning minor to scan the image light beam to generate an exami-
(Continued)

nation image light beam; and projects the examination image light beam as the examination image on a retina of an eyeball of a test subject after converging the examination image light beam in a vicinity of a pupil of the eyeball.

14 Claims, 31 Drawing Sheets

(51) Int. Cl.
*A61B 3/024* (2006.01)
*A61B 3/028* (2006.01)
*G02B 27/01* (2006.01)
*G02B 27/02* (2006.01)
*G02B 27/18* (2006.01)
*G06F 9/54* (2006.01)

(52) U.S. Cl.
CPC ............ *A61B 3/0041* (2013.01); *A61B 3/024* (2013.01); *A61B 3/028* (2013.01); *G02B 27/0172* (2013.01); *G02B 27/02* (2013.01); *G02B 27/18* (2013.01); *G06F 9/542* (2013.01); *G02B 2027/0178* (2013.01)

(58) Field of Classification Search
USPC ......................................... 351/224, 239, 246
See application file for complete search history.

(56) References Cited

U.S. PATENT DOCUMENTS

| | | | | |
|---|---|---|---|---|
| 5,737,060 | A * | 4/1998 | Kasha, Jr. ............... | A61B 3/005 351/224 |
| 5,808,589 | A * | 9/1998 | Fergason ........... | G02B 27/0172 345/8 |
| 6,068,378 | A | 5/2000 | Weiss | |
| 6,149,272 | A * | 11/2000 | Bergner ................... | A61B 3/02 351/205 |
| 6,386,706 | B1 | 5/2002 | McClure et al. | |
| 7,325,925 | B1 * | 2/2008 | Shimada ................ | A61B 3/024 351/206 |
| 7,789,510 | B2 * | 9/2010 | Fateh ..................... | A61B 3/024 351/203 |
| 8,342,684 | B2 * | 1/2013 | Ho ....................... | A61B 3/0025 351/159.79 |
| 8,657,444 | B2 * | 2/2014 | Kawamura ............ | A61B 3/032 351/224 |
| 8,888,288 | B2 * | 11/2014 | Iravani ................. | A61B 3/0033 351/223 |
| 10,058,454 | B2 * | 8/2018 | Chayet ................. | G02B 27/104 |
| 10,123,693 | B2 * | 11/2018 | Bex ....................... | A61B 3/032 |
| 10,398,310 | B2 * | 9/2019 | Swan .................... | A61B 3/1025 |
| 10,409,146 | B2 * | 9/2019 | Sugawara .............. | G02B 26/12 |
| 10,448,826 | B2 * | 10/2019 | Ito .......................... | A61B 3/024 |
| 2003/0142086 | A1 * | 7/2003 | Watanabe ............. | G02B 27/017 345/204 |
| 2004/0105073 | A1 | 6/2004 | Maddalena et al. | |
| 2009/0153796 | A1 | 6/2009 | Rabner | |
| 2010/0016730 | A1 * | 1/2010 | Tanaka .................. | A61B 3/024 600/476 |
| 2012/0002167 | A1 | 1/2012 | Kondoh | |
| 2014/0211166 | A1 | 7/2014 | Scherlen et al. | |
| 2015/0036221 | A1 * | 2/2015 | Stephenson ........ | G02B 27/0101 359/630 |
| 2017/0209044 | A1 * | 7/2017 | Ito ......................... | A61B 3/0091 |
| 2018/0020910 | A1 * | 1/2018 | Maeda ................... | A61B 3/005 351/223 |

FOREIGN PATENT DOCUMENTS

| | | |
|---|---|---|
| JP | 2004-537331 | 12/2004 |
| JP | 2009-240638 | 10/2009 |
| JP | 2009-268778 | 11/2009 |
| JP | 2010-046327 | 3/2010 |
| JP | 2010-131166 | 6/2010 |
| JP | 2012-011146 | 1/2012 |
| JP | 2013-247527 | 12/2013 |
| JP | 2014-521464 | 8/2014 |
| JP | 2014-188254 | 10/2014 |
| WO | 2010/009450 | 1/2010 |

OTHER PUBLICATIONS

International Search Report for PCT/JP2017/021211 dated Sep. 5, 2017.
Naoyuki Osaka and Koichi Oda, "Effective visual field size necessary for vertical reading during Japanese text processing", Bulletin of the Psychonomic Society, 1991, 29(4), 345-347.

* cited by examiner

| 1 | 2 | 3 | 4 | 5 | 6 | 7 | 8 | 9 | 10 |
|---|---|---|---|---|---|---|---|---|---|
| 11 | 12 | 13 | 14 | 15 | 16 | 17 | 18 | 19 | 20 |
| 21 | 22 | 23 | 24 | 25 | 26 | 27 | 28 | 29 | 30 |
| 31 | 32 | 33 | 34 | 35 | 36 | 37 | 38 | 39 | 40 |
| 41 | 42 | 43 | 44 | 45 | 46 | 47 | 48 | 49 | 50 |
| 51 | 52 | 53 | 54 | 55 | 56 | 57 | 58 | 59 | 60 |
| 61 | 62 | 63 | 64 | 65 | 66 | 67 | 68 | 69 | 70 |
| 71 | 72 | 73 | 74 | 75 | 76 | 77 | 78 | 79 | 80 |
| 81 | 82 | 83 | 84 | 85 | 86 | 87 | 88 | 89 | 90 |
| 91 | 92 | 93 | 94 | 95 | 96 | 97 | 98 | 99 | 100 |

FIG.9

| 1 | 2 | 3 | 4 | 5 | 6 |
|---|---|---|---|---|---|
| 7 | 8 | 9 | 10 | 11 | 12 |
| 13 | 14 | 15 | 16 | 17 | 18 |
| 19 | 20 | 21 | 22 | 23 | 24 |
| 25 | 26 | 27 | 28 | 29 | 30 |
| 31 | 32 | 33 | 34 | 35 | 36 |
| 37 | 38 | 39 | 40 | 41 | 42 |
| 43 | 44 | 45 | 46 | 47 | 48 |

| TEST SUBJECT ID = 001 | | |
|---|---|---|
| EXAMINATION DATE | INPUT TIME | UNREADABLE NUMBERS | READABLE NUMBERS |
| 2016/4/10 | 10:00 | 1, 2, 9-11, 20, 21, 30, 90, 100 | 3-8, 12-19, 22-29, 31-89, 91-99 |
| 2016/4/13 | 18:00 | 1, 2, 9-11, 20, 21, 30, 99, 100 | 3-8, 12-19, 22-29, 31-98 |

| TEST SUBJECT ID = 002 | | | | 331-Q |
|---|---|---|---|---|
| EXAMINATION DATE | INPUT TIME | UNREADABLE NUMBERS | READABLE NUMBERS | |
| 2016/4/10 | 10:00 | 1-4, 11-14, 21-24, 31-34, 41-44, 51-54, 60-100 | 5-10, 15-20, 25-30, 35-40, 45-50, 55-59 | |
| 2016/4/13 | 18:00 | 1-4, 11-13, 21-23, 31-33, 41-43, 51-54, 61-100 | 5-10, 14-20, 24-30, 34-40, 44-50, 55-60 | |

FIG.26

| TEST SUBJECT ID = 002 | | | 332-Q |
|---|---|---|---|
| EXAMINATION DATE | INPUT TIME | INDISCERNIBLE LANDOLT RINGS | DISCERNIBLE LANDOLT RINGS |
| 2016/4/10 | 10:00 | 1-4, 12-15, 23-26, 34-37, 45-49, 53-66 | 5-11, 16-22, 27-33, 38-44, 50-52 |

FIG.29

| TEST SUBJECT ID = 002 | | | 332A-Q |
|---|---|---|---|
| EXAMINATION DATE | INPUT TIME | INDISCERNIBLE AREA | DISCERNIBLE AREA |
| 2016/4/10 | 10:00 | (x1, y1)~(x2, y2), (x5, y5)~(x7, y7), (x10, y10)~(x15, y15) | (x3, y3)~(x4, y4), (x8, y8)~(x9, y9) |

FIG.30

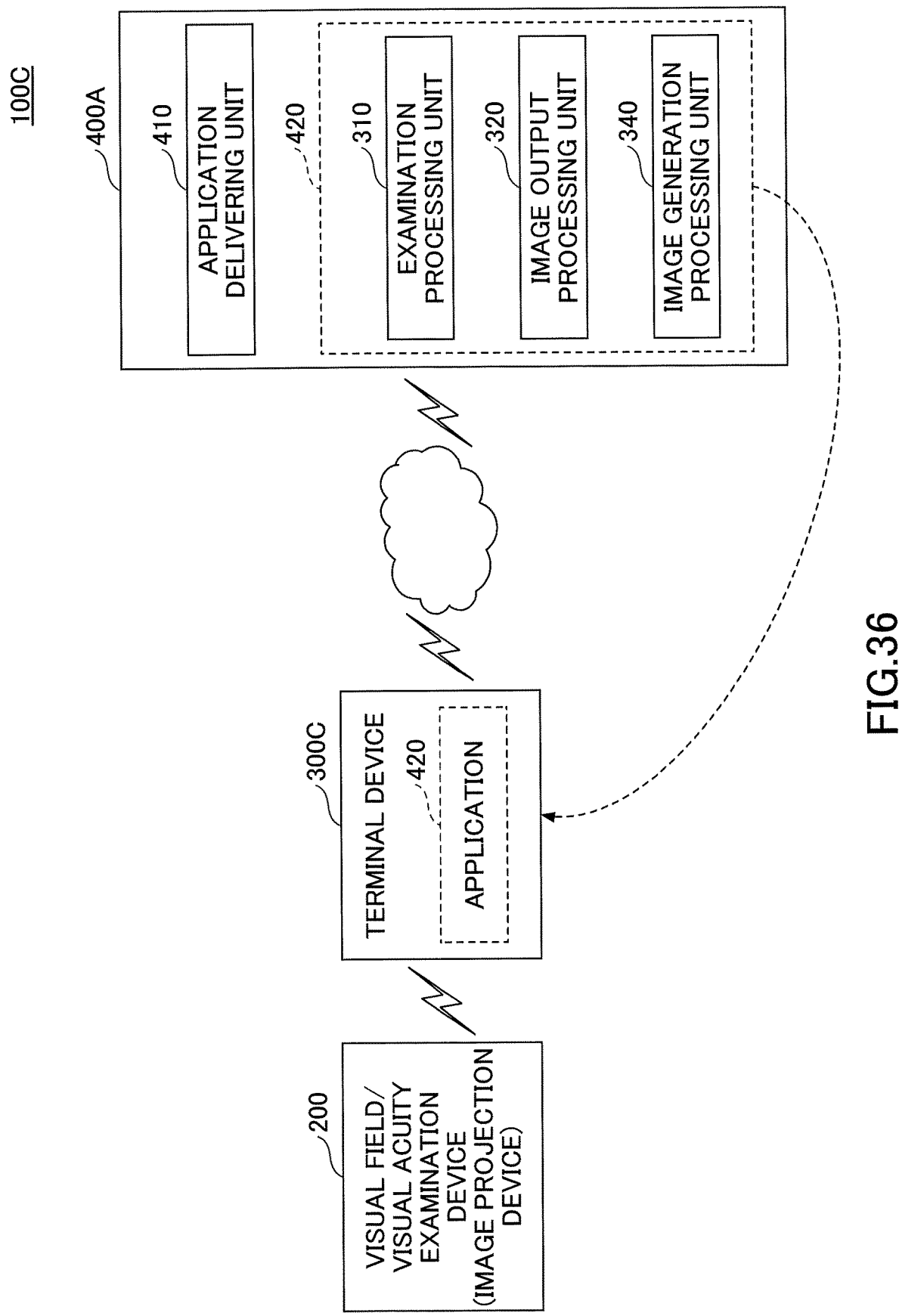

VISUAL FIELD/VISUAL ACUITY EXAMINATION SYSTEM, VISUAL FIELD/VISUAL ACUITY EXAMINATION DEVICE, VISUAL FIELD/VISUAL ACUITY EXAMINATION METHOD, VISUAL FIELD/VISUAL ACUITY EXAMINATION PROGRAM, AND SERVER DEVICE

TECHNICAL FIELD

The present invention relates to a visual field/visual acuity examination system, a visual field/visual acuity examination device, a visual field/visual acuity examination method, a visual field/visual acuity examination program, and a server device.

BACKGROUND ART

Visual field examination devices that measure the human peripheral visual field are known. Visual field examinations conducted by conventional visual field examination devices typically involve having a test subject fix his/her gaze on a fixation point, and presenting a visual target in the vicinity of the fixation point in such a state. The range of the visual field of the test subject is determined based on the test subject's response indicating whether the test subject was able to see the visual target.

Also, visual acuity examinations for measuring the visual acuity of a test subject typically involve maintaining a fixed distance between the test subject and a visual target used for visual acuity examination, and having the test subject respond by identifying the shape of the visual target.

PRIOR ART DOCUMENTS

Patent Documents

Patent Document 1: Japanese Unexamined Patent Publication No. 2003-542
Patent Document 2: Japanese Unexamined Patent Publication No. 2014-188254

SUMMARY OF THE INVENTION

Problem to be Solved by the Invention

In the conventional method for visual field examination, a flashing light dot is used as a visual target and the position at which the visual target is presented is changed from the vicinity of the fixation point to a position outside the visual field of the test subject. As such, the visual field examination takes some time. Also, in the conventional examination method, a large housing for presenting the flashing light dot to the test subject while covering the visual field of the test subject and a light-shielded space for conducting the examination are required.

Further, in the conventional method for visual acuity examination, a space in which a fixed distance can be maintained between the visual target and the test subject is required.

The disclosed technique has been conceived in view of the above problems of the related art, and it is an object of the present invention to provide a visual field/visual acuity examination system, a visual field/visual acuity examination device, a visual field/visual acuity examination method, a visual field/visual acuity examination program, and a server device that can facilitate execution of a visual field examination and a visual acuity examination.

Means for Solving the Problem

According to one embodiment of the present invention,

Advantageous Effect of the Invention

According to an aspect of the present invention, a visual field examination and a visual acuity examination can be easily performed.

BRIEF DESCRIPTION OF THE DRAWINGS

FIG. 9 is a diagram illustrating a first example of a visual field examination image according to the first embodiment;
FIG. 10 is a diagram illustrating a second example of the visual field examination image according to the first embodiment.

FIG. 23 is a first diagram illustrating an example of a visual field examination result table according to the first embodiment;

FIG. 26 is a second diagram illustrating an example of the visual field examination result table according to the first embodiment.

FIG. 29 is a first diagram illustrating an example of a visual acuity examination result table according to the first embodiment;

FIG. 30 is a second diagram illustrating an example of the visual acuity examination result table according to the first embodiment;

FIG. 36 is a diagram illustrating an example system configuration of a visual field/visual acuity examination system according to a fourth embodiment of the present invention.

EMBODIMENTS FOR IMPLEMENTING THE INVENTION

First Embodiment

Figure 1:
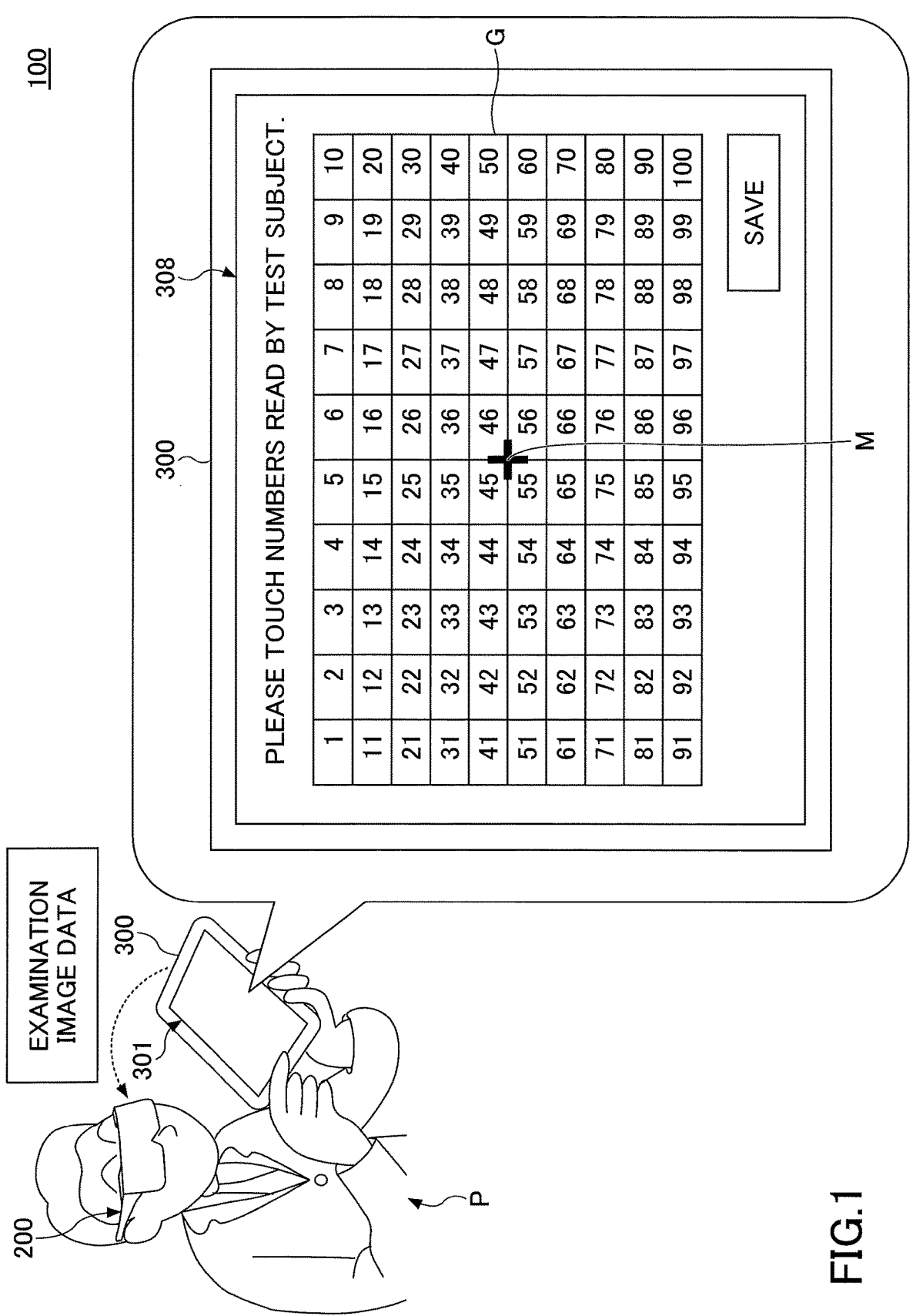
FIG. 1 is a diagram schematically illustrating a visual field examination according to a first embodiment of the present invention.

In the following, a first embodiment of the present invention will be described with reference to the drawings. A visual field/visual acuity examination system according to the present embodiment uses a terminal device and a visual field/visual acuity examination device to perform examinations, such as a visual field examination or a retinal visual acuity examination, on a test subject. First, a visual field examination according to the present embodiment will be described. FIG. 1 is a diagram schematically illustrating a visual field examination according to the first embodiment.

In a visual field/visual acuity examination system 100 according to the present embodiment, a visual field/visual acuity examination device 200 that is worn by a test subject P directly projects a visual field examination image G, which is divided into a plurality of regions, onto the retina of the test subject P. A range that can be visually perceived by the test subject P (visual field) is determined by identifying regions in the visual field examination image G that could be visually perceived by the test subject P and regions in the visual field examination image G that could not be visually perceived by the test subject P.

The visual field/visual acuity examination device 200 according to the present embodiment is a retinal projection head-mounted display using the Maxwellian view. The Maxwellian view refers to a method that involves converging image light beams based on image data at the center of the pupil before projecting the image light beams onto the retina so as to enable a person to view the image represented by the image data without being affected by the adjustment function of the person's crystalline lens.

The terminal device 300 according to the present embodiment may be a tablet computer, a smartphone, or the like, for example, and transmits image data representing the visual field examination image G to the visual field/visual acuity examination device 200. Also, the terminal device 300 according to the present embodiment displays a screen including the visual field examination image G on a display 308 to prompt input of the regions the test subject P was able to visually perceive and the regions the test subject P was unable to visually perceive. Note that the display 308 is an example of a display unit.

The visual field/visual acuity examination device 200 irradiates image light beams that are based on the image data transmitted from the terminal device 300 onto the retina of the test subject P to thereby project the visual field examination image G onto a predetermined position on the retina of the test subject P.

If the function of the retina of a person is normal, an image directly projected onto the retina of the person can be visually perceived as the image represented by the image data. However, when a person has problems in retinal function, optic nerve, or the like, the image projected onto the retina of the person is visually perceived differently from the image represented by the image data.

For example, when the retina is distorted, the image projected on the retina may be visually perceived as a distorted image according to the distortion in the retina. Also, when a portion of the visual field is lost/defective, the image projected on the retina may be visually perceived as an image having a missing portion corresponding to the lost/defective portion of the visual field.

As described above, when there is some abnormality in the retina or optic nerve, for example, an image projected on the retina will not be visually perceived exactly as the image being represented. In other words, if there is some abnormality in visual perception, the abnormality is reflected in the image that is visually perceived when perceiving an image projected onto the retina.

In this respect, according to an aspect of the present embodiment, the visual field of a test subject is determined by identifying, from an examination image projected onto the retina of the test subject, regions of the examination image that could be visually perceived and regions of the examination image that could not be visually perceived by the test subject.

More specifically, in the visual field/visual acuity examination system 100 according to the present embodiment, the visual field examination image G has a fixation point M provided at the center, and the visual field examination image G is divided into a plurality of regions, with each region having an identifier (character) for identifying the region inscribed therein.

According to an aspect of the present embodiment, the test subject P is prompted to fixate on the fixation point M of the visual field examination image G that is displayed on the display 308 of the terminal device 300, and is prompted to input a region from which the test subject P was able to read the inscribed character (identifier) and a region from which the test subject was unable to read the inscribed character.

That is, in the present embodiment, the input to the terminal device 300 corresponds to the visual field examination result of the test subject P.

Thus, according to an aspect of the present embodiment, because the Maxwellian view is used, the visual field examination image G can be projected directly onto a predetermined position on the retina, and the test subject P only has to visually perceive the visual field examination image G that has been projected onto the retina of the test subject P. That is, even if the test subject P slightly moves his/her gaze, the examination image can be prevented from moving on the retina of the test subject P. Further, according to an aspect of the present embodiment, the visual field can be determined by simply having the test subject look at the visual field examination image G without having to gradually change the presentation position of a flashing light dot used as a visual target, for example, and in this way, the examination time can be substantially reduced.

Also, according to an aspect of the present embodiment, a light-shielded space or a large housing for covering the visual field of the test subject is not necessary, and as such, the visual field examination can be performed at any location.

As described above, according to an aspect of the present embodiment, the burden on the test subject can be reduced. Further, according to an aspect of the present embodiment, a large housing that is conventionally used is not necessary such that the visual field examination can be easily performed with a simple configuration.

Note that in the example of FIG. 1, the visual field/visual acuity examination device 200 has the shape of a general eyeglass, but the present invention is not limited thereto. For example, the visual field/visual acuity examination device 200 may have the shape of a goggle covering both eyes of the test subject P.

Also, in the case where the test subject P inputs the visual field examination result in the terminal device 300, the test subject P may input the visual field examination result after removing the visual field/visual acuity examination device 200, or the test subject P may input the visual field examination result while looking at the visual field examination image G displayed on the display 308 of the terminal device 300 using the eye that is not being examined, for example.

Also, in the case where it is difficult for the test subject P to input the examination result to the terminal device 300 while wearing the visual field/visual acuity examination device 200, the test subject P may ask an examination assistant to input the examination result to the terminal device 300. In this case, for example, the test subject P may communicate to the examination assistant the regions from which the test subject P was able to read the inscribed characters by reading out the characters that the test subject P was able to visually perceive. Further, in a case where the terminal device 300 includes an audio input unit (e.g. microphone) and an audio recognition function, for example, the test subject P may read out the characters that the test subject P was able to visually perceive, and the audio of the test subject P may be directly input to the terminal device 300 as the examination result.

Figure 2:
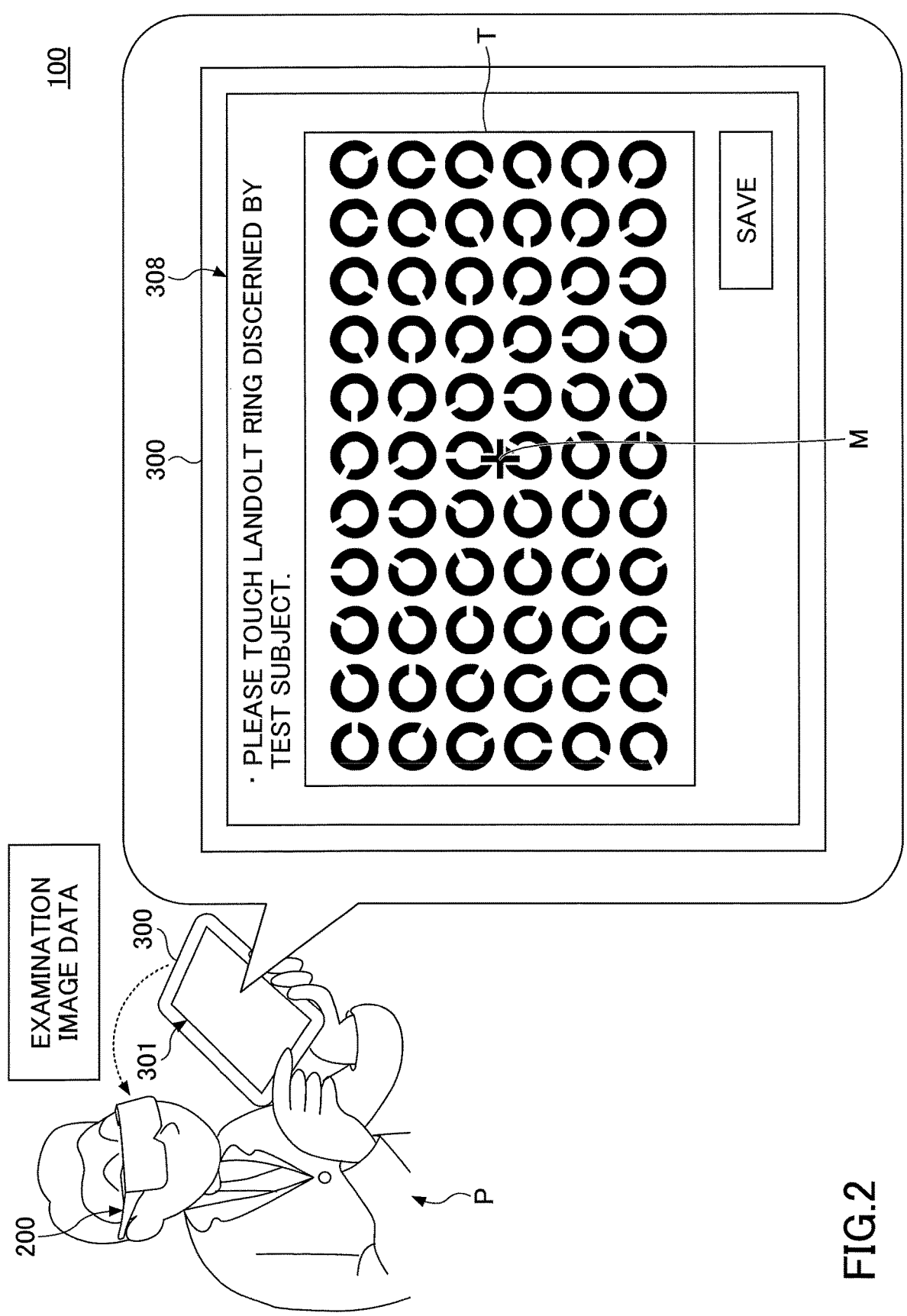
FIG. 2 is a diagram illustrating a visual acuity examination according to the first embodiment.

In the following, a visual acuity examination according to the present embodiment will be described. FIG. 2 is a diagram illustrating the visual acuity examination according to the first embodiment.

When performing a visual acuity examination in the visual field/visual acuity examination system 100 according to the present embodiment, the terminal device 300 transmits image data representing a visual acuity examination image T to the visual field/visual acuity examination device 200. Also, the terminal device 300 according to the present embodiment causes the display 308 to display a screen including the visual acuity examination image T to prompt input of the visual acuity examination result of the test subject P.

In the visual acuity examination, the visual field/visual acuity examination device 200 according to the present embodiment similarly irradiates image light beams based on the image data transmitted from the terminal device 300 onto the retina of the test subject P as described above in connection with the visual field examination. In this way, the visual field/visual acuity examination device 200 projects the visual acuity examination image T onto a predetermined position on the retina of the test subject P.

As shown in FIG. 2, the visual acuity examination image T according to the present embodiment has a fixation point M provided at the center and a plurality of Landolt rings arranged vertically and the horizontally. Note that the visual acuity examination image T according to the present embodiment includes a plurality of images having Landolt rings in varying sizes.

In the present embodiment, as shown in FIG. 2, the visual acuity examination image T is directly projected onto the retina of the test subject P so that the visual acuity of the retina itself of the test subject P can be measured.

The visual acuity of the retina itself refers to the function of the macula of the retina, which is different from general visual acuity, for example, which varies depending on thickness adjustment of the crystalline lens by the ciliary muscle and the like.

For example, the larger the size of the Landolt ring in the visual acuity examination image T from which a gap position can be discerned, the lower the visual acuity of the retina, and the smaller the size of the Landolt ring in the visual acuity examination image T from which the gap position can be discerned, the higher the visual acuity of the retina.

As described above, in the present embodiment, the visual acuity of the retina itself that is not affected by the crystalline lens or the like can be measured. As such, the present embodiment can be used, for example, for prediction of the degree of recovery of visual acuity when the crystalline lens is replaced with an artificial lens due to disease such as cataract.

In the visual acuity examination by the visual field/visual acuity examination system 100 according to the present embodiment, for example, the test subject P may communicate to the examination assistant the positions of the gaps in the Landolt rings in the visual acuity examination image T projected onto the retina while the test subject P is wearing the visual field/visual acuity examination device 200. In turn, the examination assistant may input the examination result to the terminal device 300 by operating the display 308 to select the Landolt rings for which the test subject P was able to accurately discern the gap positions from among the Landolt rings in the visual acuity examination image T, for example.

In the following, the devices included in the visual field/visual acuity examination system 100 according to the present embodiment will be described with reference to FIGS. 3 to 6.

Figure 3:
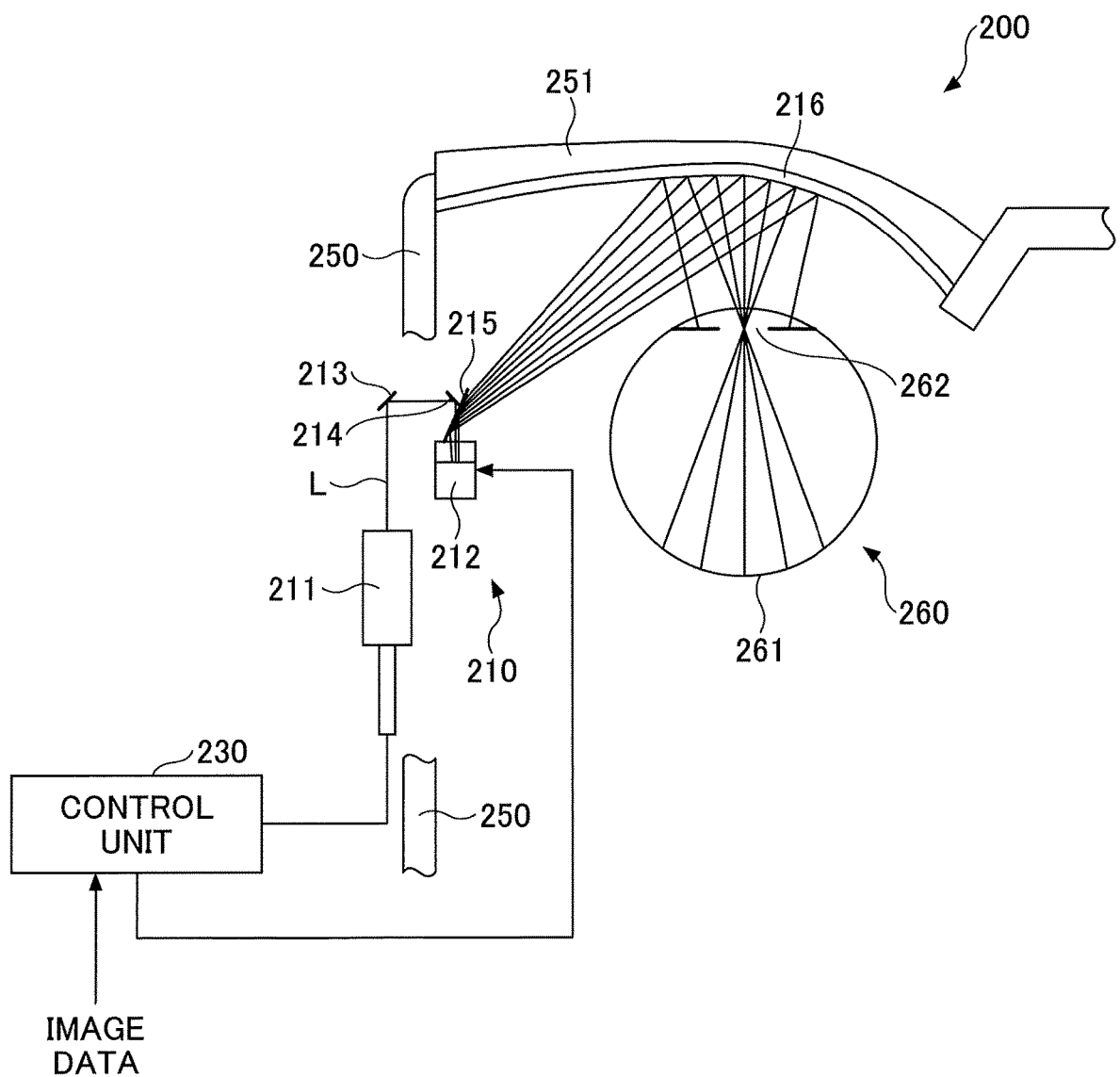
FIG. 3 is a top view of a visual field/visual acuity examination device.

FIG. 3 is a top view of the visual field/visual acuity examination device 200. The visual field/visual acuity examination device 200 according to the present embodiment includes a projection unit 210 and a control unit 230.

The projection unit 210 according to the present embodiment includes a light source 211, a scanning mirror 212, a mirror 213, a mirror 214, a mirror 215, and a projection unit 216.

The light source 211 is disposed at a temple (arm) 250 of an eyeglass frame. The light source 211 emits a light beam L having a single wavelength or a plurality of wavelengths, for example, under the direction of the control unit 230. This light beam L is an image light beam for projecting an image onto the retina 261 of the eyeball 260 of a user. In the following description, the light beam L is referred to as an image light beam.

The light source 211 may be configured to emit red laser light (wavelength: about 610 nm to 660 nm), green laser light (wavelength: about 515 nm to 540 nm), and blue laser light (wavelength: about 440 nm to 480 nm), for example. The light source 211 according to the present embodiment may be implemented by a light source having laser diode chips of RGB (red, green, blue), a three-color synthesizing device, and a micro collimating lens integrated therein, for example.

The scanning mirror 212 is disposed at the temple 250 of the eyeglass frame. The scanning mirror 212 scans the image light beam emitted from the light source 211 in the horizontal direction and the vertical direction. The scanning mirror 212 may be a MEMS (Micro Electro Mechanical System) mirror, for example. Note that the image light beam emitted from the light source 211 may be reflected by the mirror 213 and the mirror 214 to be incident on the scanning mirror 212, for example.

The control unit 230 according to the present embodiment may be implemented by a processor, such as a CPU (Central Processing Unit), and a memory, such as a RAM (Random Access Memory) and a ROM (Read Only Memory), for example.

The processor and the memory may be mounted on the same substrate as the substrate on which the scanning mirror 212 (MEMS mirror) is mounted, for example. Further, the processor and the memory may be provided in an external device (e.g., the terminal device 300) that is connected to the visual field/visual acuity examination device 200.

The control unit 230 according to the present embodiment controls the projection unit 210. The control unit 230 causes an image light beam based on input image data to be emitted from the light source 211. Further, the control unit 230 according to the present embodiment causes the scanning mirror 212 (MEMS mirror) to vibrate and scan the image light beam emitted from the light source 211 and cause an image to be projected on the retina 261.

Note that the visual field/visual acuity examination device 200 according to the present embodiment may have the components shown in FIG. 3 provided on both the left and right sides of the eyeglass frame, for example. Alternatively, the components shown in FIG. 3 other than the control unit 230 may be provided on both the left and right sides of the eyeglass frame, and the control unit 230 may be configured to control both the left and right side components, for example. Also, according to an aspect of the present embodiment, the components shown in FIG. 3 may be provided on either the left side or the right side of the eyeglass frame. In this case, for example, when the visual field test of the left eye is performed, the visual field/visual acuity examination device 200 having the components of FIG. 3 provided on the left side of the eyeglass frame may be used, and when the visual field examination of the right eye is performed, the visual field/visual acuity examination device 200 having the components of FIG. 3 provided on the right side may be used.

In the following, projection of an image by the projection unit 210 of the visual field/visual acuity examination device 200 will be described with reference to FIGS. 4 and 5.

Figure 4:
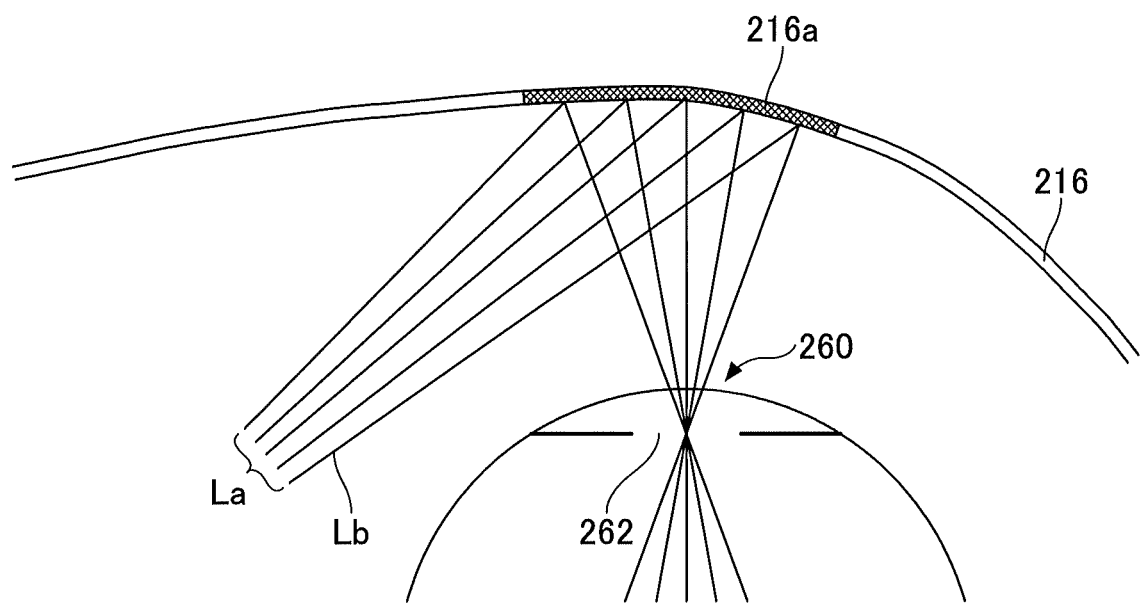
FIG. 4 is an enlarged view of the vicinity of a projection portion of the visual field/visual acuity examination device.

FIG. 4 is an enlarged view of the vicinity of a projection portion of the visual field/visual acuity examination device 200.

As shown in FIGS. 3 and 4, the image light beams scanned by the scanning mirror 212 is reflected by the mirror 215 and directed toward a lens 251 of the eyeglass frame. In the present embodiment, the projection unit 210 is disposed on a surface toward the eyeball 260 side of the lens 251, and as such, the image light beams scanned by the scanning mirror 212 are incident on the projection unit 216.

An area 216a of the projection unit 216 on which the light beams are incident is a half mirror having a free-form surface or a combined structure of a free-form surface and a diffractive surface. In this way, the image light beams incident on the projection unit 216 converge in the vicinity of the pupil 262 of the eyeball 260 and are then projected onto the retina 261.

Thus, the test subject can perceive an image formed by the image light beams and also visually perceive an image of the outside world in a see-through manner.

Figure 5:
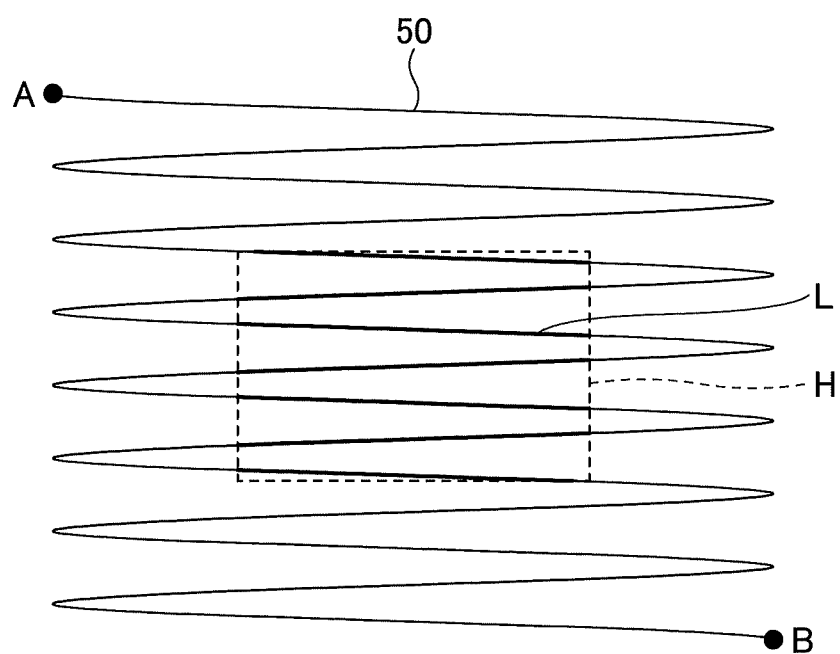
FIG. 5 is a diagram illustrating vibration of a first mirror.

FIG. 5 is a diagram illustrating vibration of a first mirror. Note that FIG. 5 illustrates an example case where the scanning mirror 212 vibrates to scan an image light beam from point A to point B.

An example method of scanning an image light beam with the scanning mirror 212 and projecting an image onto the retina 261 includes a method of rapidly scanning light from the upper left to the lower right of an image projection area to thereby display an image (e.g., raster scan).

In the present embodiment, as shown in FIG. 5, in order to scan the image light beam (light beam L), the scanning mirror 212 moves across a larger range in the horizontal direction (first direction) and the vertical direction (second direction intersecting with the first direction) as compared with an image projection area H (a range indicated by broken lines in FIG. 5) corresponding to an area on the retina 261 onto which an image is to be projected. In FIG. 5, the vibration of the scanning mirror 212 is indicated by reference numeral 50.

In the case where an image is projected onto the retina 261 by scanning the image light beam at a location where deflection of the scanning mirror 212 is substantially large, distortion of the image increases. Thus, in the present embodiment, the image light beam is scanned at a location where the deflection of the scanning mirror 212 is small.

Note that although FIG. 5 illustrates an example case where an image light beam is scanned across a rectangular shape, the present invention is not limited to such a case, and the image light beam may be scanned across a trapezoidal shape or some other shape, for example.

Also, in the present embodiment, the size of the image projection area H onto which an image is projected is preferably large enough to cover the visual field of the test subject. A size covering the visual field of the test subject may be, for example, a size that allows an image projected onto the retina to cover approximately 60° nasally and superiorly, approximately 70° inferiorly, and approximately 90°-100° temporally (laterally).

According to an aspect of the present embodiment, by setting the area onto which an image (examination image) is to be projected to be in a size covering the visual field of the test subject, appropriate visual field examination can be conducted even with respect to a test subject having no abnormality in the visual field, retina, optic nerve, or the like.

Note that with respect to a test subject that is known to have a defect in a portion of the visual field, the image projection area H onto which an image is to be projected may be arranged to be smaller than the above-described size of "approximately 60° nasally and superiorly, approximately 70° inferiorly, and approximately 90°-100° temporally".

Figure 6:
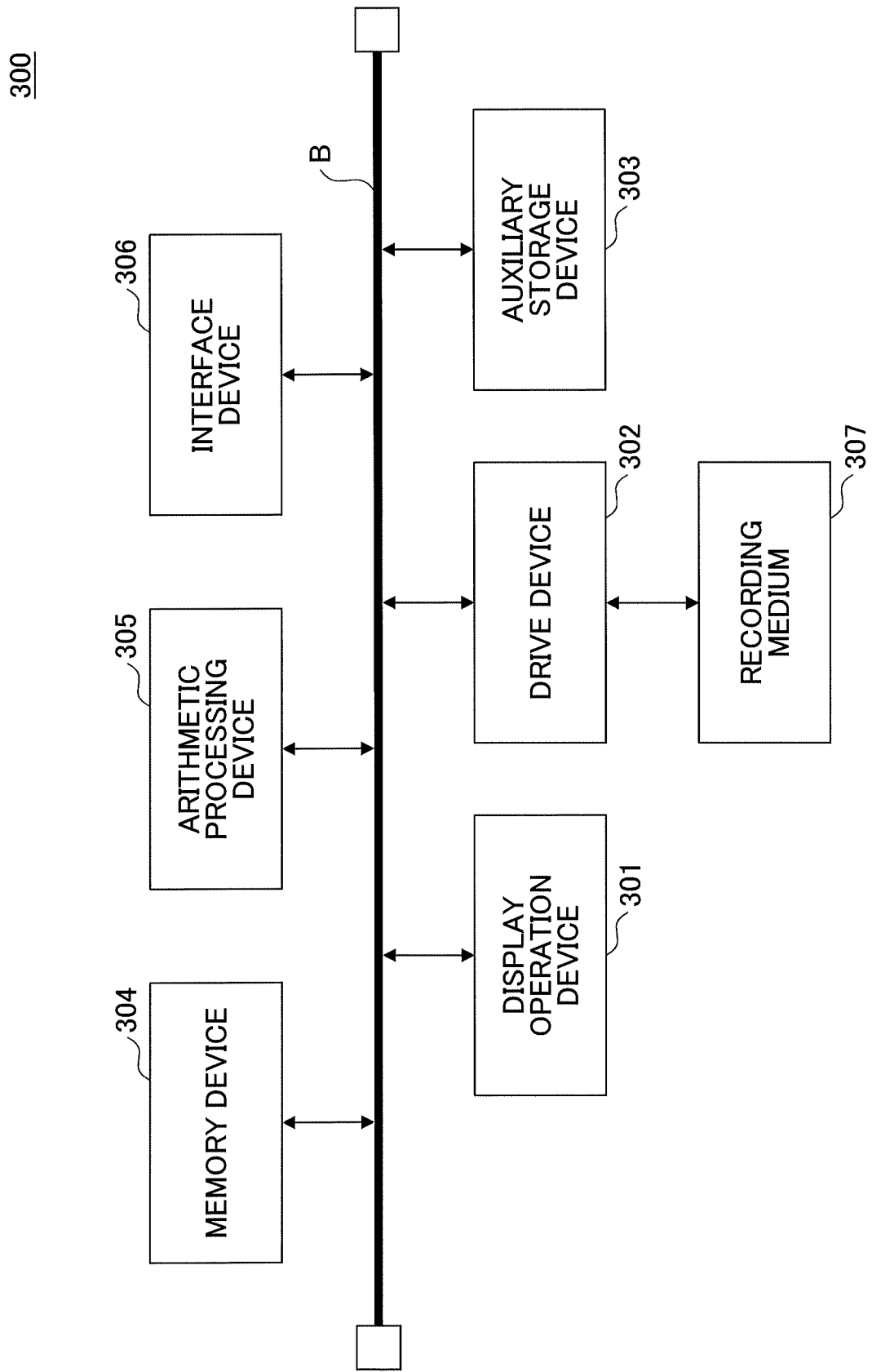
FIG. 6 is a diagram illustrating an example hardware configuration of a terminal device.

In the following, the terminal device 300 according to the present embodiment will be described. FIG. 6 is a diagram illustrating an example hardware configuration of the terminal device 300.

The terminal device 300 according to the present embodiment includes a display operation device 301, a drive device 302, an auxiliary storage device 303, a memory device 304, an arithmetic processing device 305, and an interface device 306 that are connected to each other by a bus B.

The display operation device 301 may be a touch panel or the like, and has a display function for displaying information and an input function for inputting information. The interface device 306 may include a LAN card, for example, and is used for establishing connection with a network.

A visual field/visual acuity examination program to be executed by the terminal device 300 constitutes at least a part of various programs for controlling the terminal device 300. The visual field/visual acuity examination program may be recorded in a recording medium 307 and distributed, downloaded from a network, or provided in some other suitable manner. Note that various types of recording media may be used as the recording medium 307 storing the visual field/visual acuity examination program including a recording medium for optically, electrically or magnetically recording information, such as a CD-ROM, a flexible disk, a magneto-optical disk, and the like; and a semiconductor memory for electrically recording information such as a ROM or a flash memory, for example.

Also, when the recording medium 307 storing the visual field/visual acuity examination program is loaded in the drive device 302, the visual field/visual acuity examination program stored in the recording medium 307 may be installed in the auxiliary storage device 303 via the drive device 302. The visual field/visual acuity examination program that is downloaded from a network may be installed in the auxiliary storage device 303 via the interface device 306.

The auxiliary storage device 303 stores the installed visual field/visual acuity examination program and stores necessary files, data, and the like. The memory device 304 reads the visual field/visual acuity examination program from the auxiliary storage device 303 and stores the read visual field/visual acuity examination program when the terminal device 300 is activated. The arithmetic processing device 305 implements various processes as described below based on the visual field/visual acuity examination program stored in the memory device 304.

Note that although the terminal device 300 according to the present embodiment includes the display operation device 301, embodiments of the present invention are not limited thereto. For example, the terminal device 300 may be implemented by a desktop computer, a laptop computer, or the like. In such case, instead of including the display operation device 301, the terminal device 300 may include an input device for inputting information, such as a mouse or a keyboard, and an output device such as a display for displaying information.

Figure 7:
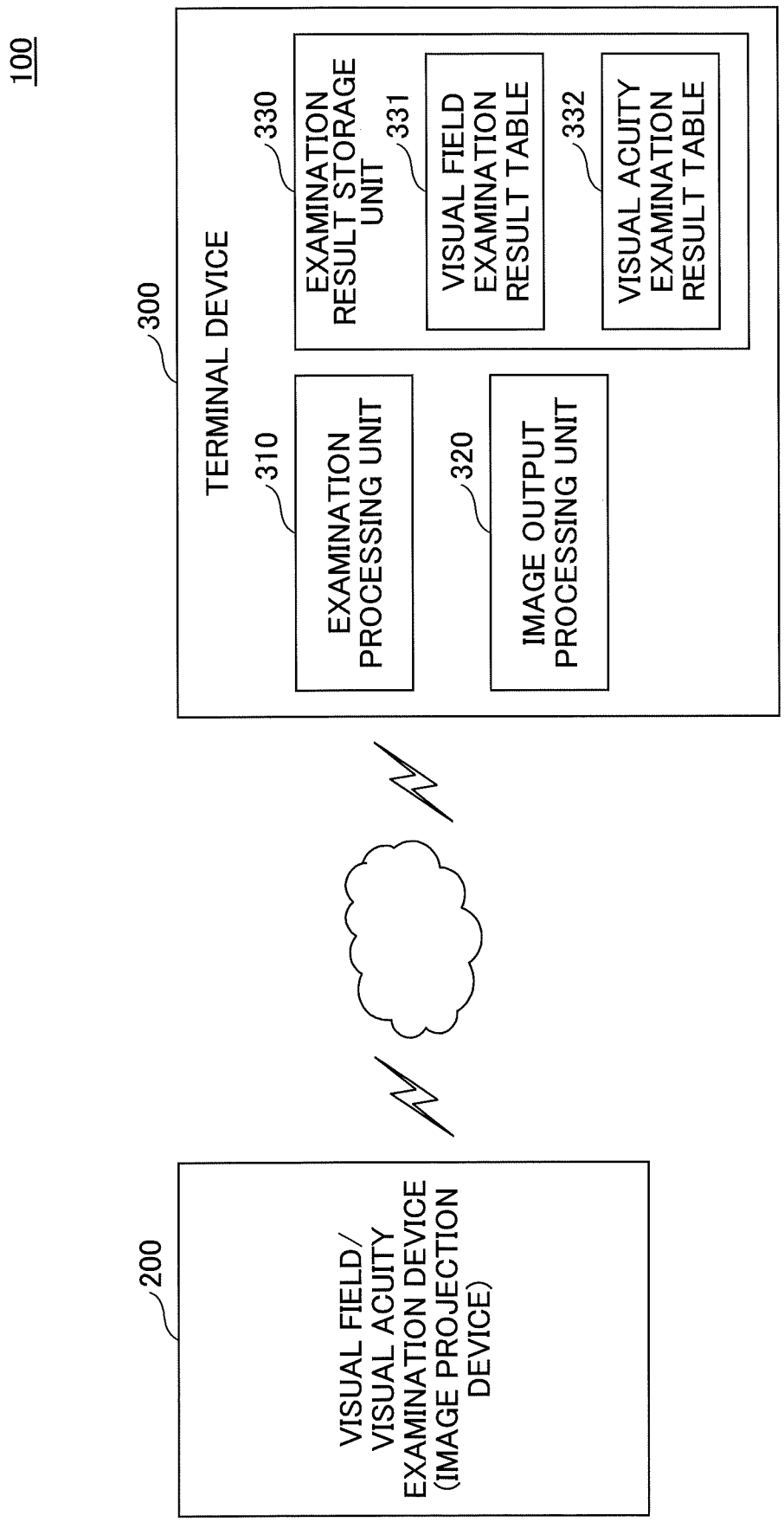
FIG. 7 is a diagram illustrating an example system configuration of a visual field/visual acuity examination system according to the first embodiment.

In the following, the visual field/visual acuity examination system 100 according to the present embodiment will be described with reference to FIG. 7. FIG. 7 is a diagram illustrating an example system configuration of the visual field/visual acuity examination system 100 according to the first embodiment.

The visual field/visual acuity examination system 100 according to the present embodiment includes the visual field/visual acuity examination device 200 and the terminal device 300. In the visual field/visual acuity examination system 100, the visual field/visual acuity examination device 200 is connected to the terminal device 300 and communicates with the terminal device 300.

In the example of FIG. 7, the visual field/visual acuity examination device 200 and the terminal device 300 communicate wirelessly, but the present invention is not limited thereto. The visual field/visual acuity examination device 200 and the terminal device 300 may be connected in any manner as long as they are capable of communicating with each other.

The terminal device 300 according to the present embodiment includes an examination processing unit 310, an image output processing unit 320, and an examination result storage unit 330.

The examination processing unit 310 according to the present embodiment holds examination image data corresponding to the visual field examination image G and image data corresponding to the visual acuity examination image T, and passes these sets of examination image data to the image output processing unit 320.

Also, the examination processing unit 310 according to the present embodiment displays the visual field examination image G or the visual acuity examination image T on its own device screen, accepts an input of an examination result of a test subject, and stores examination result information indicating the examination results in the examination result storage unit 330. Note that the examination processing unit 310 will be described in detail below.

The image output processing unit 320 outputs the image data received from the examination processing unit 310 to an external device. Specifically, the image output processing unit 320 according to the present embodiment outputs (transmits) the visual field examination image data and the visual acuity examination image data to the visual field/visual acuity examination device 200.

The examination result storage unit 330 includes a visual field examination result table 331 and a visual acuity examination result table 332. The visual field examination result table 331 stores a visual field examination result of a test subject wearing the visual field/visual acuity examination device 200. The visual acuity examination result table 332 stores a visual acuity examination result of a test subject wearing the visual field/visual acuity examination device 200. Note that the visual field examination result table 331 and the visual acuity examination result table 332 will be described in detail below.

Figure 8:
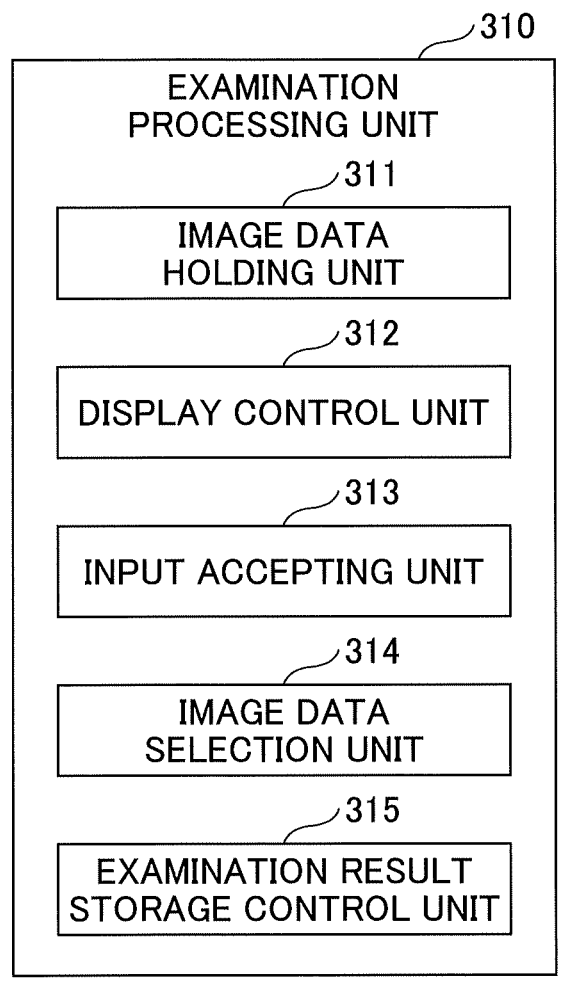
FIG. 8 is a diagram illustrating an examination processing unit according to the first embodiment.

In the following, the examination processing unit 310 according to the present embodiment will be described with reference to FIG. 8. FIG. 8 is a diagram illustrating the examination processing unit according to the first embodiment. Note that the units shown in FIG. 8 may be implemented by the arithmetic processing device 305 of the terminal device 300 reading and executing the visual field/visual acuity program stored in the memory device 304, for example.

The examination processing unit 310 according to the present embodiment includes an image data holding unit 311, a display control unit 312, an input accepting unit 313, an image data selection unit 314, and an examination result storage control unit 315.

The image data holding unit 311 holds visual field examination image data corresponding to the visual field examination image G and visual acuity examination image data corresponding to the visual acuity examination image T. Upon accepting an examination start request, the image data holding unit 311 according to the present embodiment passes relevant examination image data according to the examination to be executed to the image output processing unit 320 and the display control unit 312.

Note that although the examination image data is only held by the image data holding unit 311 in the visual field/visual acuity examination system 100 according to the present embodiment, the present invention is not limited thereto. For example, the examination image data may also be held by the control unit 230 of the visual acuity examination device 200.

Upon receiving examination image data, the display control unit 312 controls the display 308 of the terminal device 300 to display an examination result input screen including the examination image represented by the examination image data. More specifically, the display control unit 312 may control the display 308 to display an examination result input screen including the visual field examination image G or an examination result input screen including the visual acuity examination image T. Also, the display control unit 312 according to the present embodiment may display an examination selection screen for selecting the visual field examination or the visual acuity examination in response to receiving an examination execution request, for example.

The input accepting unit 313 accepts inputs according to various operations performed at the display operation device 301. Specifically, the input accepting unit 313 may accept an examination start request, a selection of an examination to be performed, an input to an examination result input screen, and the like.

The image data selection unit 314 selects examination image data corresponding to the type of examination specified in an input accepted by the input accepting unit 313 from among the examination image data held in the image data holding unit 311 and passes the selected examination image data to the display control unit 312.

Specifically, when the visual field examination is selected at the examination selection screen, the image data selection unit 314 selects the examination image data corresponding to the visual field examination image G and passes the selected examination image data to the display control unit 312. When the visual acuity examination is selected at the examination selection screen, the image data selection unit 314 selects the examination image data corresponding to the visual acuity examination image T and passes the selected examination image data to the display control unit 312.

The examination result storage control unit 315 stores the examination result accepted by the input accepting unit 313 in the examination result storage unit 330 in association with information on the test subject and information indicating the date/time the input of the examination result was accepted.

In the following, the visual field examination image G will be described with reference to FIGS. 9 and 10. FIG. 9 is a diagram illustrating a first example of the visual field examination image according to the first embodiment. FIG. 10 is a diagram illustrating a second example of the visual field examination image according to the first embodiment.

The visual field examination image G shown in FIG. 9 is vertically and horizontally divided into a plurality of regions. In other words, the visual field examination image G is made up of a group of rectangular regions.

Each region of the visual field examination image G has a number of the Arabic numeral system inscribed therein as an identifier for identifying the region. Note, however, that the identifier for identifying the region is not limited to a number of the Arabic numeral system. For example, a number of some other numeral system, a hiragana character, a kanji character, a letter of the alphabet, or a character/letter of some other language may be used as the identifier of the region.

Also, in the visual field examination image G, a fixation point M is formed at a center portion. In the example of FIG. 9, the mark "+" is used as a mark indicating the fixation point M. However, the shape of the mark indicating the fixation point is not limited this example. That is, the shape of the mark indicating the fixation point may be any shape as long as it can indicate to the test subject P the point to which the test subject P should fix his/her gaze.

Among the various types of visual impairments, in some types of visual impairments, a person may be able to distinguish images but not characters. According to an aspect of the present embodiment, a character may be used as the identifier of each region of the examination image so that the ability to recognize each character indicated in each region can be determined, for example.

Note that although the above-described effect can be achieved by using a character as the identifier of each region in the present embodiment, the identifier does not necessarily have to be a character. For example, an image may be displayed in each region as the identifier of the region.

For example, in the visual field examination image shown in FIG. 9, an image of an apple may be displayed in the region with the identifier "1", and an image of a car may be displayed in the region with the identifier "2". Also, for example, an image of a star-shaped mark may be displayed in the region with the identifier "1", and an image of a heart-shaped mark may be displayed in the area with the identifier "2", for example.

By using an image rather than a character as the identifier of each region as described above, for example, the visual field examination image may be used even with respect to a test subject that does not have the ability to recognize characters to determine regions that are visible to the test subject and regions that are not visible to the test subject.

Note that although the visual field examination image G shown in FIG. 9 includes 100 regions, the number of regions included in the visual field examination image G is not limited thereto. The number of regions in the visual field examination image G may be determined according to the size of the area onto which the visual field examination image G is to be projected. Also, the number of regions in the visual field examination image G may be adjusted so that regions that are visible to a test subject and regions that are not visible to the test subject can be determined.

When the number of regions included in the visual field examination image G is too large, the visual field examination may be burdensome to the test subject, and when the number of regions is too small, regions that are visible to the test subject and regions that are not visible to the test subject may not be properly determined. As such, in the present embodiment, the number of regions in the visual field examination image G is preferably set up so that regions visible to the test subject and regions not visible to the test subject can be properly determined without unduly increasing the burden on the test subject. For example, the number of regions may be determined in advance based on results of repeatedly performing visual field examinations using the visual field/visual acuity examination system 100 according to the present embodiment.

Note that although the regions included in the visual field examination image G according to the present embodiment are rectangular regions, the present invention is not limited thereto. For example, the shape of the regions included in the visual field examination image G may be circular, elliptical, or square.

FIG. 10 shows a visual field examination image G1 that has identifiers in different sizes inscribed in the plurality of regions; i.e., the greater the distance of a region from the fixation point M at the center, the larger the size of the identifier inscribed therein.

In a visual field examination, when the test subject P fixates on the fixation point at the center of the visual field examination image G1, the identifiers in the regions near the fixation point can be easily perceived by the test subject P, whereas the identifiers in the regions farther away from the fixation point become harder to perceive by the test subject P.

Thus, in the visual field examination image G1, an identifier located farther away from the fixation point M as the center is indicated in a larger size so that visibility of the identifiers at the periphery of the visual field examination image G1 can be improved. Note that the visual field examination image G1 may also be used to measure the visual acuity distribution of the retina itself, for example.

Figure 11:
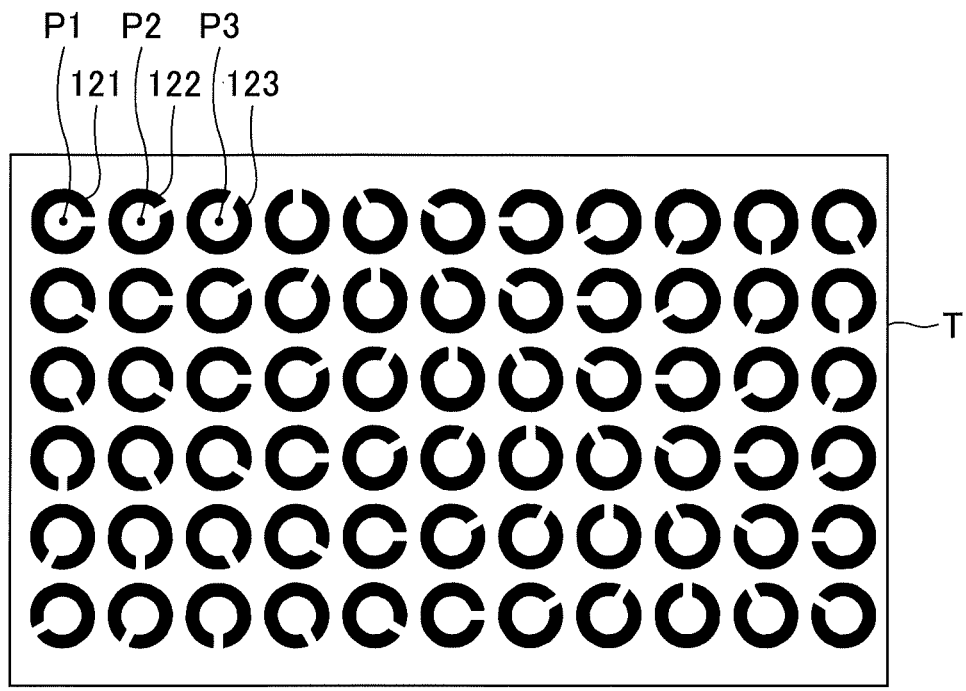
FIG. 11 is a first diagram illustrating an example of a visual acuity examination image according to the first embodiment.

In the following, the visual acuity examination image will be described with reference to FIGS. 11 to 18. FIG. 11 is a first diagram showing an example of the visual acuity examination image according to the first embodiment.

In the visual acuity examination image T shown in FIG. 11, Landolt rings are arranged into 6 rows and 11 columns. According to an aspect of the present embodiment, coordinates indicating the center of each Landolt ring included in the visual acuity examination image T may be associated with the visual acuity examination image T.

For example, assuming the visual acuity examination image T was displayed on a visual acuity examination result input screen (see FIG. 2), and the test subject was unable to discern the gaps in the Landolt rings 121 to 123 in the visual acuity examination image T, in the present embodiment, the coordinates of the respective center points P1, P2, P3 of the Landolt rings 121, 122, and 123 may be output as information identifying the Landolt rings for which the user could not discern the gaps.

Figure 12:
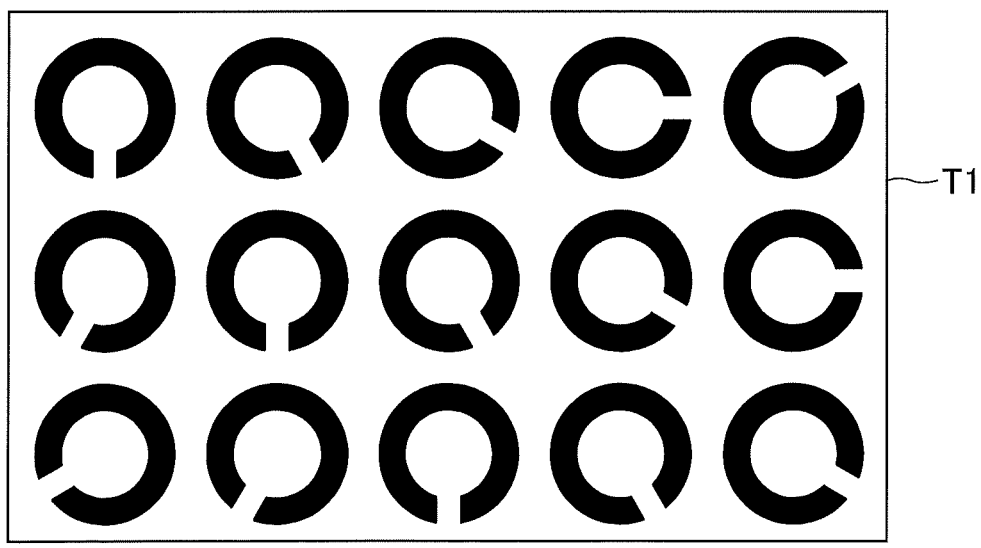
FIG. 12 is a second diagram illustrating an example of the visual acuity examination image according to the first embodiment.

FIG. 12 is a second diagram showing an example of the visual acuity examination image according to the first embodiment. In the visual acuity examination image T1 shown in FIG. 12, Landolt rings are arranged into 3 rows and 5 columns. As can be appreciated, the Landolt rings in the visual acuity examination image T1 are larger than the Landolt rings in the visual acuity examination image T shown in FIG. 11.

In the present embodiment, visual acuity examination images having Landolt rings in various sizes for various levels of visual acuity are provided in addition to the example visual acuity examination images shown in FIGS. 11 and 12.

In the present embodiment, the size of the Landolt rings to be projected onto the retina of a test subject may be selected according to the visual acuity of the test subject, and a visual acuity examination image displaying Landolt rings in the selected size may be projected onto the retina of the test subject. Note that the size of the Landolt rings to be projected onto the retina of the test subject may be selected by the test subject or the examination assistant, for example.

In the present embodiment, by changing the size of the Landolt rings of the visual acuity examination image T in small increments or continuously, the visual acuity, expressed in decimal notation, may be measured up to two decimal places.

Figure 13:
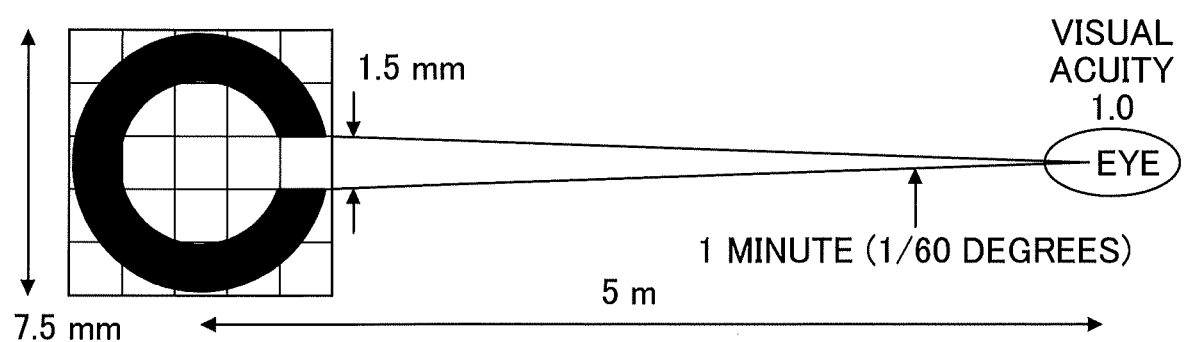
FIG. 13 is a diagram illustrating a Landolt ring.

In the following, the Landolt ring will be described with reference to FIG. 13. FIG. 13 is a diagram showing a Landolt ring.

The Landolt ring is a black circular ring, and the ratio of the diameter of the circular ring to the stroke width of the circular arc to the width of the ring opening (the gap width) is set to 5:1:1.

In the present embodiment, for example, when a gap of about 1.45 mm can be discerned from a distance of 5 m, the visual acuity is determined to be 1.0. More specifically, a person with the ability to determine the position of the gap in a Landolt ring with a diameter of 7.5 mm, a stroke width of 1.5 mm, and a gap width of 1.5 mm upon viewing the Landolt ring from a distance of 5 m may be deemed to have a visual acuity of "1.0".

Thus, in the present embodiment, for example, in the case of measuring whether a test subject has a visual acuity of 1.0 or more, the visual field/visual acuity examination device 200 may be used to project onto the retina of the test subject, a visual acuity examination image T including a Landolt ring in a size corresponding to the size of a Landolt ring with a diameter of 7.5 mm, a stroke width of 1.5 mm, and a gap width of 1.5 mm viewed from a distance of 5 m.

Figure 14:
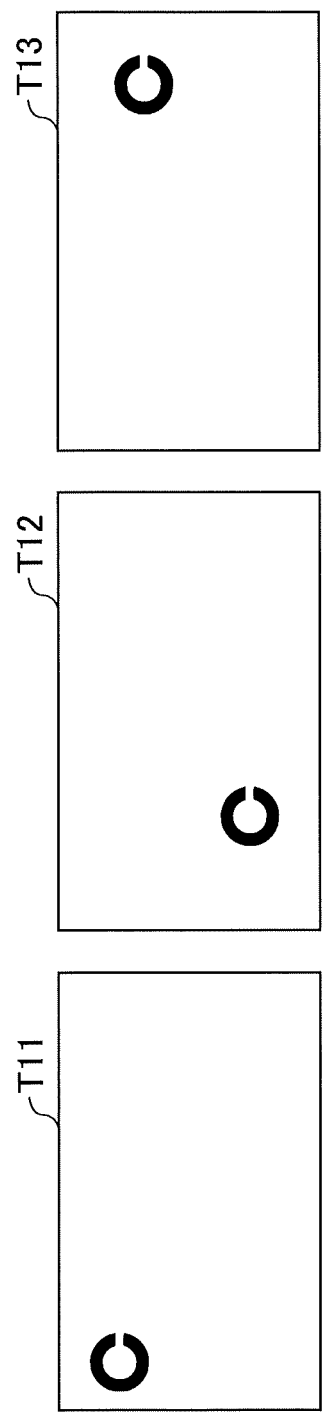
FIG. 14 is a third diagram illustrating an example of the visual acuity examination image according to the first embodiment.

FIG. 14 is a third diagram showing an example of the visual acuity examination image according to the first embodiment.

In the example of FIG. 14, visual acuity examination images with Landolt rings arranged at different positions are shown. In FIG. 14, a visual acuity examination image T11 has one Landolt ring arranged at the upper left side, and a visual acuity examination image T12 has one Landolt ring arranged at the lower left side. Also, a visual acuity examination image T13 shown in FIG. 14 has one Landolt ring arranged at the upper right side.

According to an aspect of the present embodiment, by sequentially projecting visual acuity examination images having Landolt rings arranged at different positions as shown in FIG. 14 on the retina of a test subject, the presence/absence of defects in the visual field of the test subject may be examined in addition to examining the visual acuity of the test subject.

Note that although one visual acuity examination image is arranged to have one Landolt ring arranged therein in the example of FIG. 14, the present invention is not limited thereto. That is, a plurality of Landolt rings may be arranged in one visual acuity examination image.

Also, although visual acuity examination images having Landolt rings arranged at different positions are sequentially projected onto the retina of the user in the example of FIG. 14, the present invention is not limited thereto. For example, a visual acuity examination image may be projected onto the retina of the user as a moving image in which the position of the Landolt ring moves.

By using visual acuity examination images as described above, in the present embodiment, the visual field and the visual acuity of a test subject may be associated with each other. In other words, according to an aspect of the present embodiment, the distribution of visual acuity in the retina of the test subject may be determined.

Figure 15:
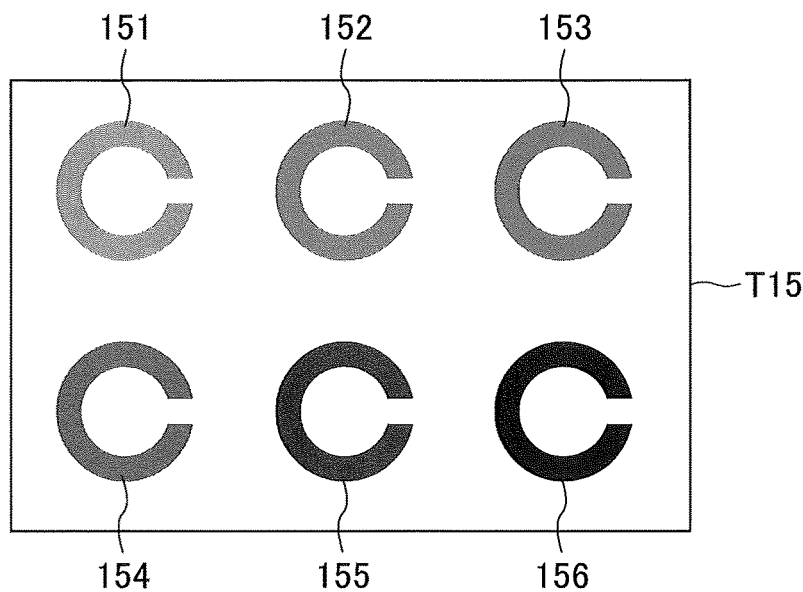
FIG. 15 is a fourth diagram illustrating an example of the visual acuity examination image according to the first embodiment.

FIG. 15 is a fourth diagram showing an example of the visual acuity examination image according to the first embodiment. The visual acuity examination image T15 shown in FIG. 15 has a plurality of Landolt ring images 151 to 156 in different luminance levels arranged therein.

In the visual acuity examination image T15, the luminance level gradually decreases from the Landolt ring image 151 toward the Landolt ring image 156.

According to an aspect of the present embodiment, by changing the luminance level of Landolt ring images, the luminance required for the user to discern an image may be determined.

Note that in the visual acuity examination image according to the present embodiment, the Landolt ring may be a black image, or may be an image of a color other than black, such as blue, red, or green, for example. According to an aspect of the present embodiment, by changing the color of the Landolt ring images, the presence/absence of abnormalities in color vision may be examined in addition to examining the visual acuity.

Figure 16:
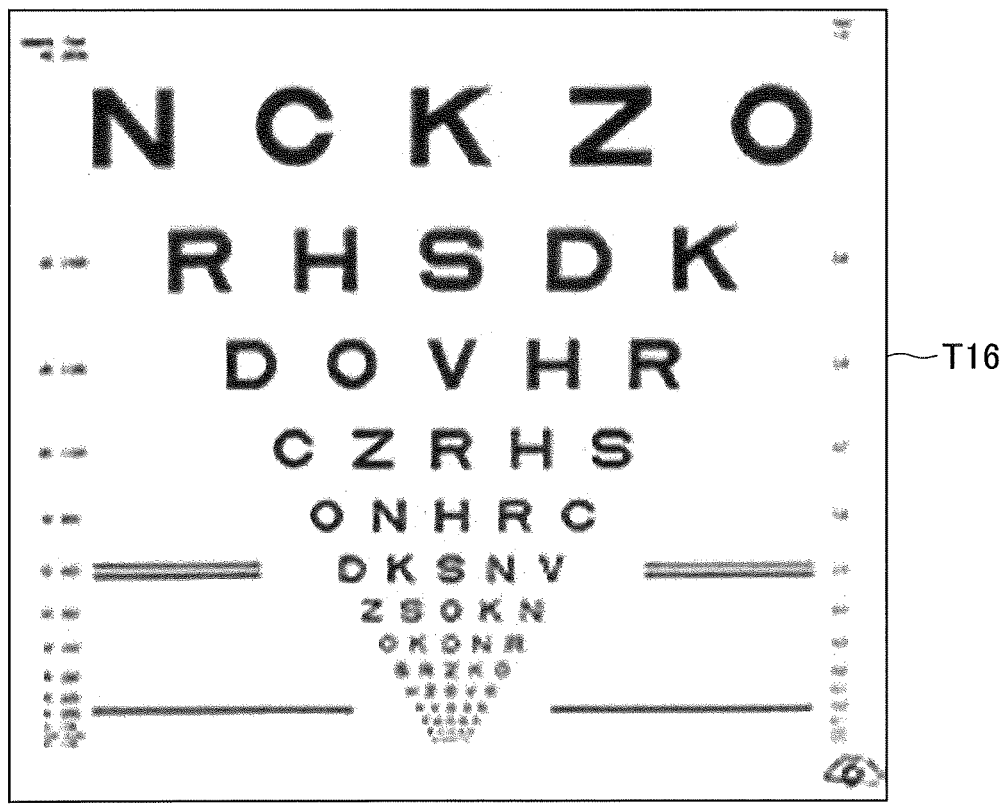
FIG. 16 is a fifth diagram illustrating an example of the visual acuity examination image according to the first embodiment.

FIG. 16 is a fifth diagram showing an example of the visual acuity examination image according to the first embodiment. According to an aspect of the present embodiment, a visual acuity examination may be conducted using images other than Landolt ring images.

The visual acuity examination image T16 shown in FIG. 16 includes an ETDRS (Early Treatment of Diabetic Retinopathy Study) chart.

In the ETDRS chart, five visual targets are arranged in one line, and the visual target size differences between the lines are in 0.1 log MAR units. Also, characters corresponding to the visual targets are Sloan letters 10 characters of C, D, H, K, N, O, R, S, V, Z) in the Sloan font. In the ETDRS chart, the space between the visual targets is equal to the size of one visual target, and letter-by-letter scoring is performed rather than line-by-line scoring.

As described above, according to an aspect of the present embodiment, a visual acuity examination may be conducted using a visual target other than the Landolt ring. In addition to the ETDRS chart, a visual target other than the Landolt ring may include a tumbling E chart, for example.

Figure 17:
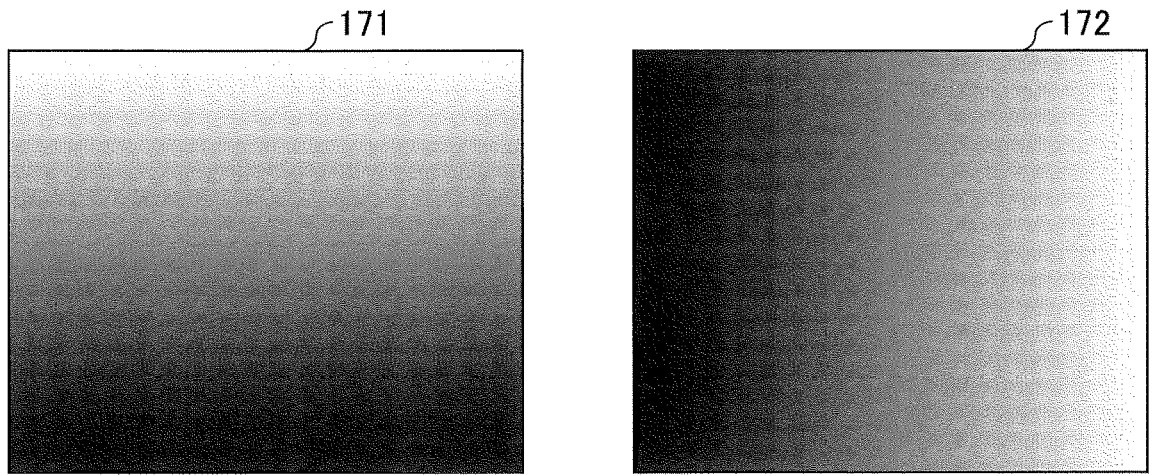
FIG. 17 is a diagram illustrating an example of an image used for contrast sensitivity examination.
Figure 28:
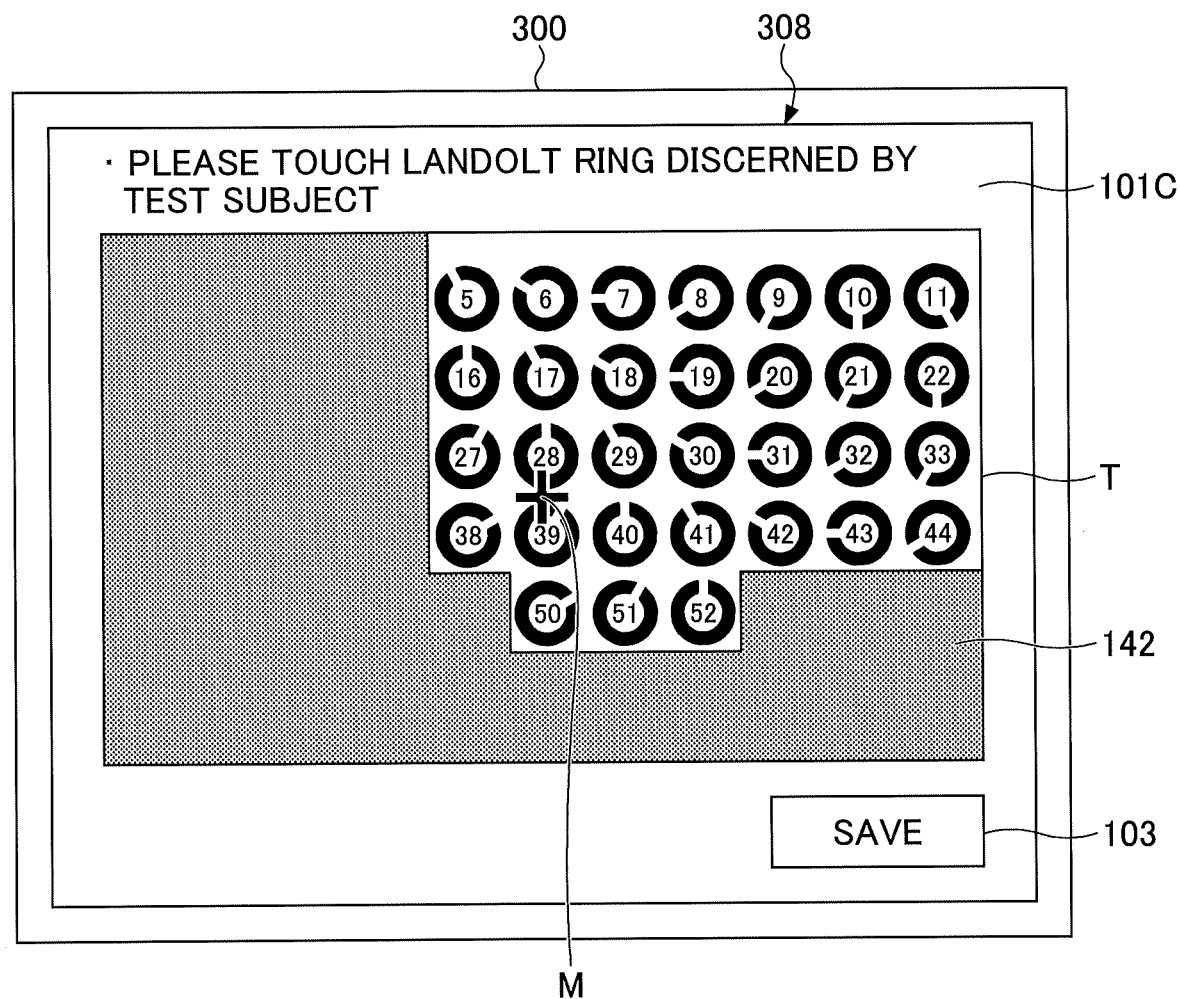
FIG. 28 is a diagram illustrating an example of a visual acuity examination result input screen having a visual acuity examination result input thereto according to the first embodiment.

FIG. 17 is a diagram showing example images used for examining contrast sensitivity, and FIG. 28 is a diagram showing example images used for examining astigmatism.

The visual acuity examination image T according to the present embodiment may include an image for examining contrast sensitivity as shown in FIG. 17, for example.

The images 171 and 172 shown in FIG. 17 are used for projecting color gradations onto the entire visual field. According to an aspect of the present embodiment, the contrast sensitivity of a test subject can be measured by projecting a color gradation image onto the visual field of the test subject and inputting the color that can be perceived by the test subject as an examination result.

Note that according to an aspect of the present embodiment, a plurality of images for projecting the same color onto the entire visual field may be prepared instead of a color gradation image, and the plurality of images may be sequentially projected to implement a color gradation.

Figure 18:
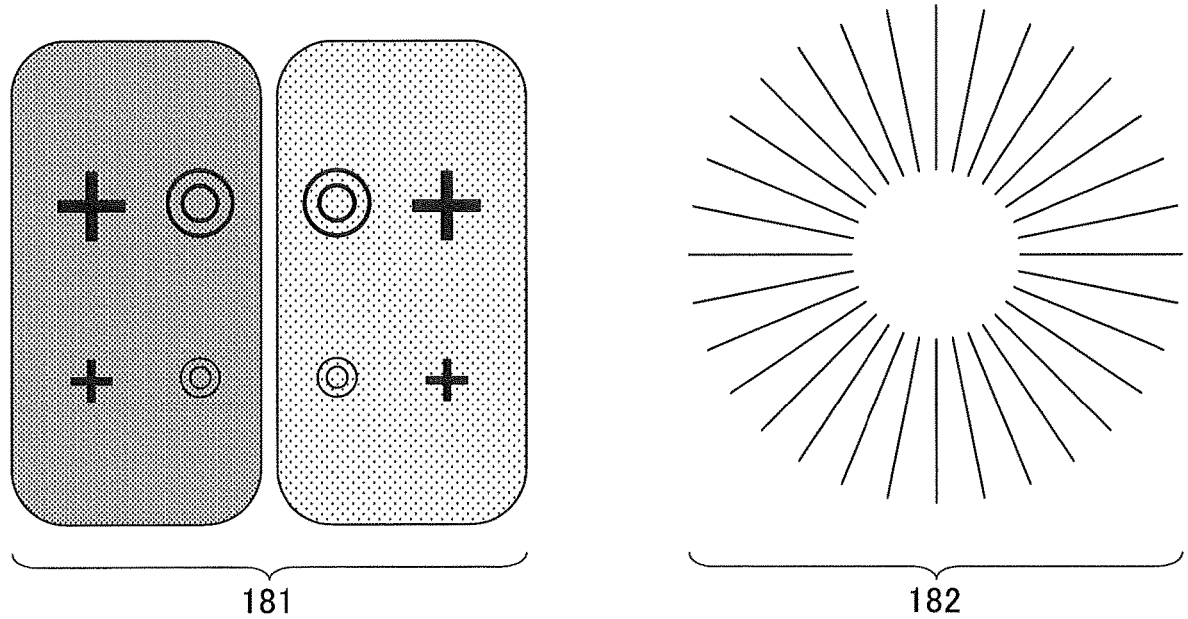
FIG. 18 is a diagram showing an example of an image used for astigmatism examination.

Also, the visual acuity examination image T according to the present embodiment may include an image 181 and an image 182 for examining astigmatism as shown in FIG. 18, for example. By including these images in the visual acuity examination image T, a test subject may also be examined for astigmatism.

Figure 19:
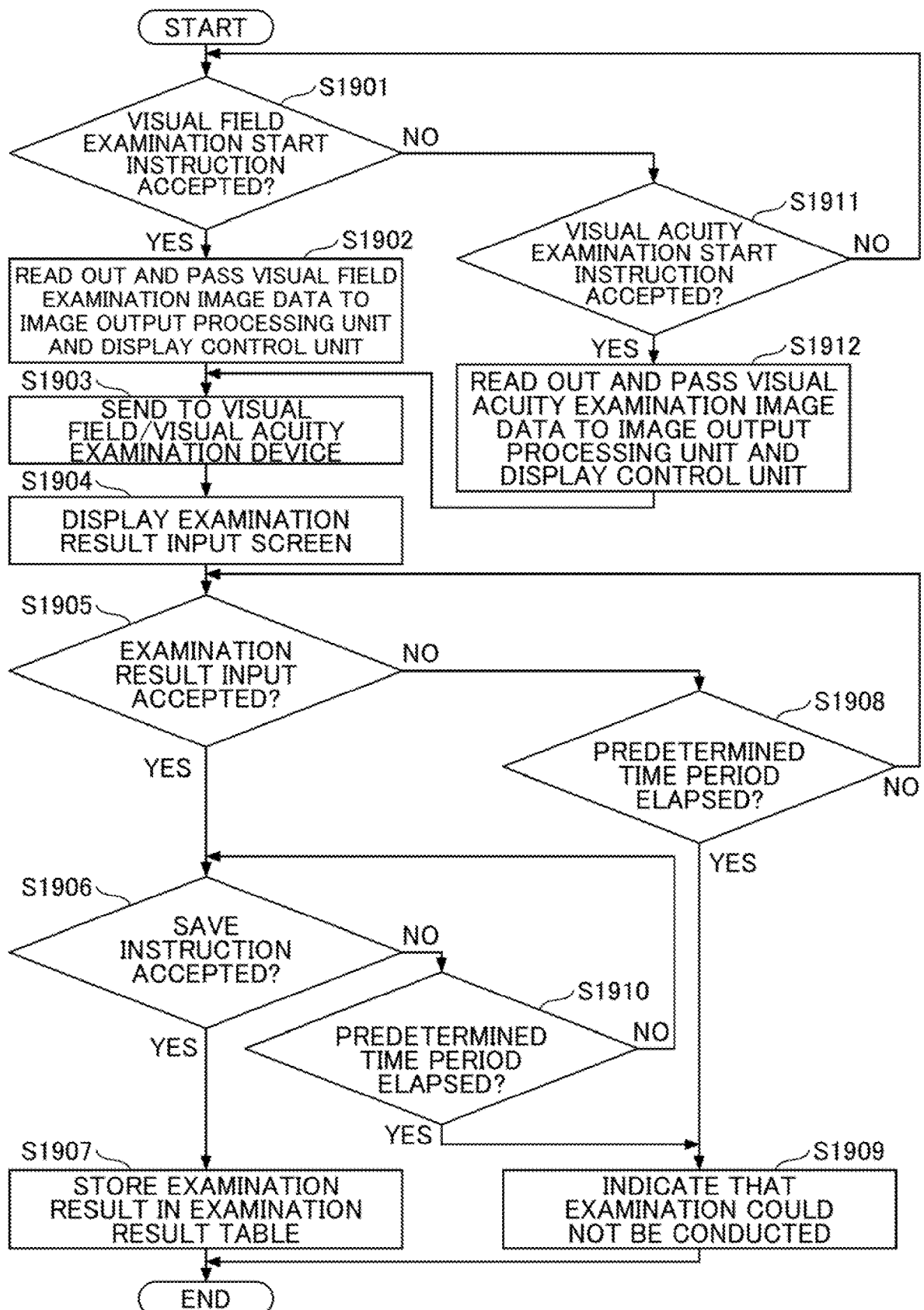
FIG. 19 is a flowchart illustrating example process operations of the terminal device according to the first embodiment.

In the following, process operations of the terminal device 300 according to the present embodiment will be described with reference to FIG. 19. FIG. 19 is a flowchart illustrating example process operations of the terminal device according to the first embodiment.

In the terminal device 300 according to the present embodiment, the examination processing unit 310 determines whether the input accepting unit 313 has accepted a visual field examination start request (step S1901). Upon determining, in step S1901, that a visual field examination start request has not been accepted, the examination processing unit 310 proceeds to step S1911, which will be described below.

Upon accepting a visual field examination start request in step S1901, the image data selection unit 314 of the examination processing unit 310 selectively reads the visual field examination image data from among the examination image data held by the image data holding unit 311 and passes the selected visual field examination image data to the image output processing unit 320 and the display control unit 312 (step S1902).

The image output processing unit 320 transmits the visual field examination image data to the visual field/visual acuity examination device 200 (step S1903). In the visual field/visual acuity examination device 200, when the transmitted examination image data is input to the control unit 230, the projection unit 210 scans an image light beam based on the input examination image data onto the retina of a test subject so that the test subject can visually perceive the visual field examination image G.

The display control unit 312 controls the display 308 of the terminal device 300 to display an examination result input screen including the visual field examination image G based on the examination image data (step S1904). Note that the examination result input screen will be described in detail below.

Then, in the examination processing unit 310, the input accepting unit 313 determines whether an input of an examination result has been accepted at the examination result input screen (step S1905). Upon determining, in step S1905, that an input of an examination result has not been accepted, the input accepting unit 313 proceeds to step S1908, which will be described below.

Upon accepting an input of an examination result in step S1905, the input accepting unit 313 determines whether a save instruction for saving the examination result has been accepted (step S1906). Upon determining, in step S1906, that a save instruction has not been accepted, the input accepting unit 313 proceeds to step S1910, which will be described below.

Upon accepting an input of a save instruction in step S1906, the examination result storage control unit 315 of the examination processing unit 310 stores the input examination result in the examination result storage unit 330 (step S1907), and the examination processing unit 310 ends the process.

Upon determining, in step S1905, that an input of an examination result has not been accepted, the input accepting unit 313 determined whether a predetermined time period has elapsed (step S1908). Upon determining, in step S1908, that the predetermined time period has not elapsed, the input accepting unit 313 returns to step S1905.

Upon determining that the predetermined time period has elapsed in step S1908, the display control unit 312 of the examination processing unit 310 causes the terminal device 300 to display a notification that the visual field examination could not be properly conducted (step S1909), and the examination processing unit 310 ends the process.

Upon determining, in step S1906, that a save instruction has not been accepted, the input accepting unit 313 determines whether a predetermined period has elapsed (step S1910). Upon determining, in step S1910, that the predetermined time has not elapsed, the input accepting unit 313 returns to step S1906.

Upon determining that the predetermined time period has elapsed in step S1910, the examination processing unit 310 proceeds to step S1909.

Also, upon determining, in step S1901, that a visual field examination start request has not been accepted, the examination processing unit 310 according to the present embodiment determines whether a visual acuity examination start request has been accepted by the input accepting unit 313 (step S1911). Upon determining, in step S1911, that a visual acuity examination start request has not been accepted, the examination processing unit 310 returns to step S1901.

Upon determining that a visual acuity examination start request has been accepted in step S1911, the image data selection unit 314 of the examination processing unit 310 selectively reads the visual acuity examination image data from the examination image data held by the image data holding unit 311 and passes the selected visual acuity examination image data to the image output processing unit 320 and the display control unit 312 (step S1912), and the process proceeds to step S1903.

Figure 20:
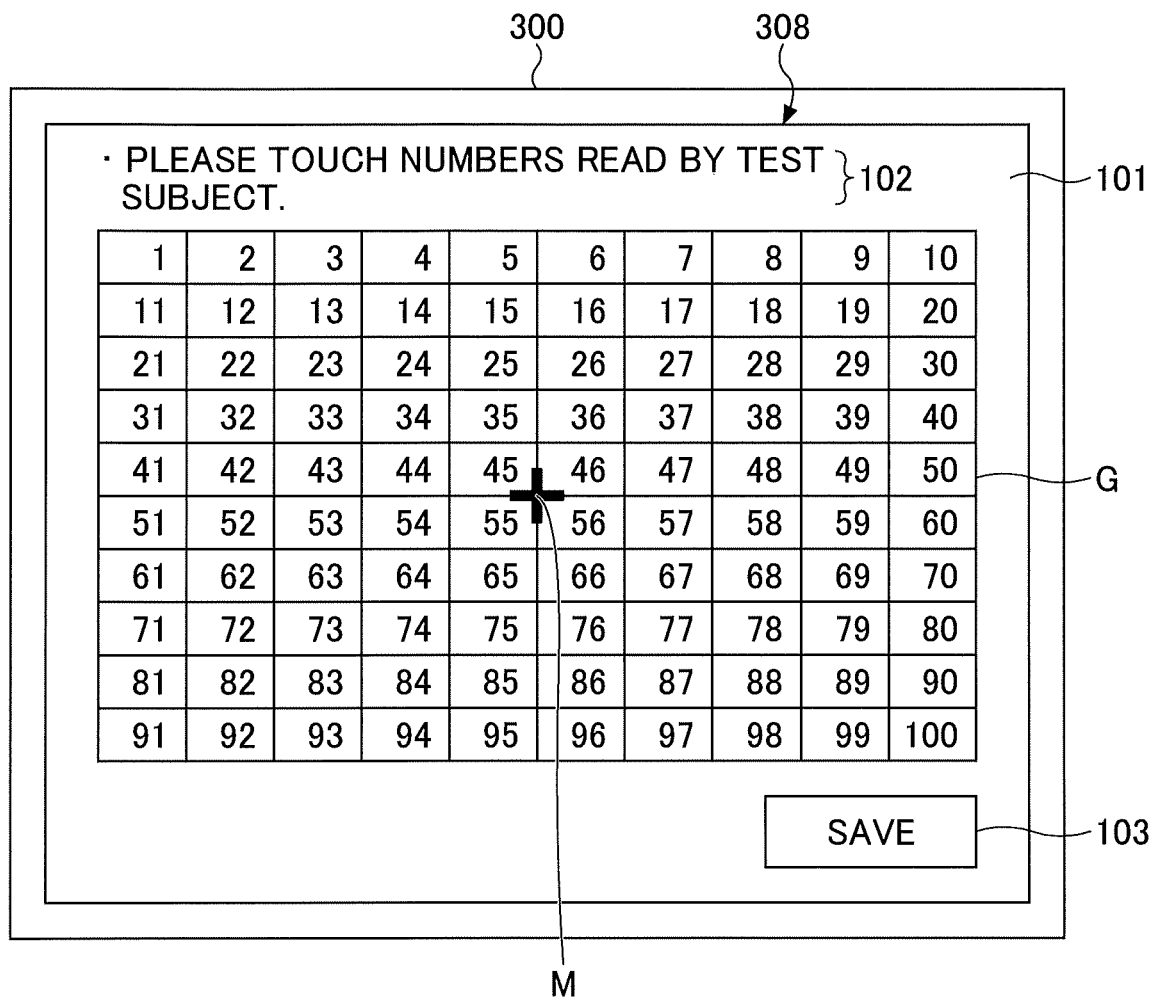
FIG. 20 is a diagram illustrating an example of a visual field examination result input screen according to the first embodiment.

In the following, the examination result input screen will be described with reference to FIG. 20. FIG. 20 is a diagram showing an example of the examination result input screen according to the first embodiment. The examination result input screen 101 shown in FIG. 20 is displayed on the display 308 of the terminal device 300.

The examination result input screen 101 includes the visual field examination image G. Further, the examination result input screen 101 includes a message 102 prompting selection of a number that could be read in the visual field examination image G, and a button 103 for instructing the terminal device 300 to save the examination result.

Note that in the example of FIG. 20, the message 102 indicates "Please touch numbers read by test subject" to prompt selection of the numbers in the visual field examination image G that could be visually perceived by the test subject. However, the present invention is not limited to this example. For example, the message 102 may alternatively indicate content prompting selection of numbers in the visual field examination image G that could not be visually perceived by the test subject.

The content of the message 102 may be set up in advance by an administrator of the visual field/visual acuity examination system 100, for example. Also, whether to select readable numbers or unreadable numbers may be set up by the test subject, for example.

In the following, the examination result storage unit 330 according to the present embodiment will be described with reference to FIGS. 21A to 26. First, a visual field examination result table 331-P storing a visual field examination result of the test subject P will be described with reference to FIGS. 21 to 23.

Figure 21A:
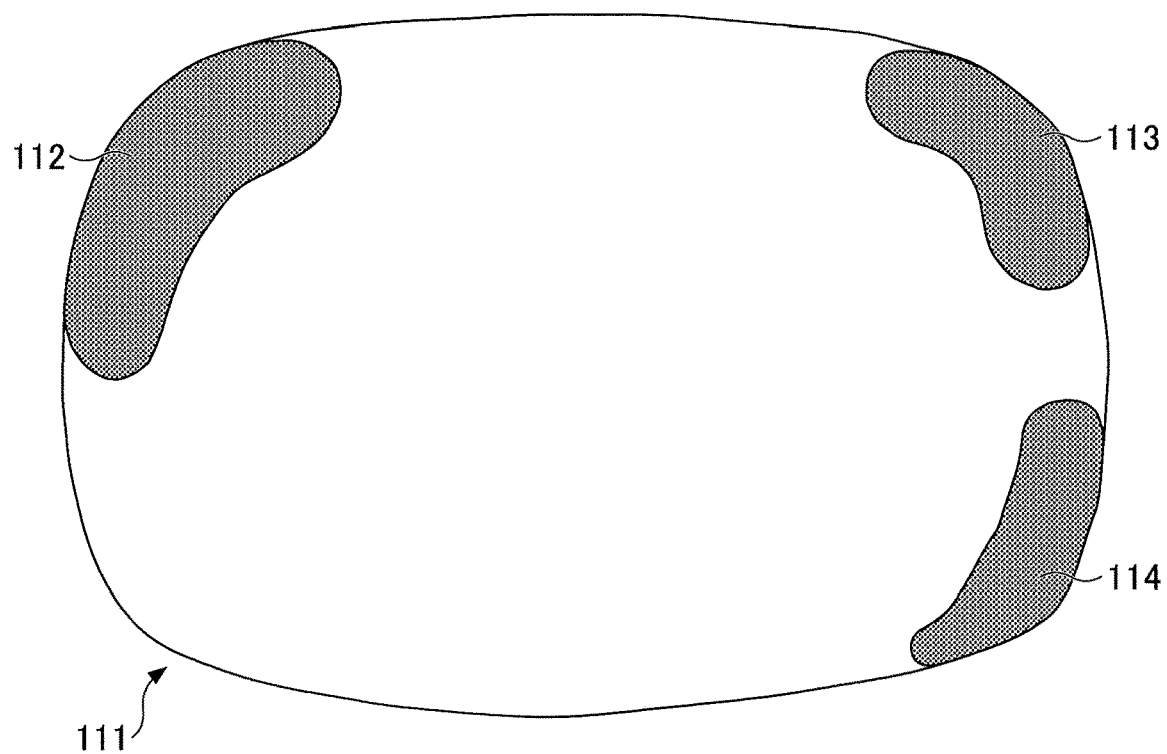
FIG. 21A is a diagram illustrating an example view of the visual field examination image as viewed by a test subject P.
Figure 21B:
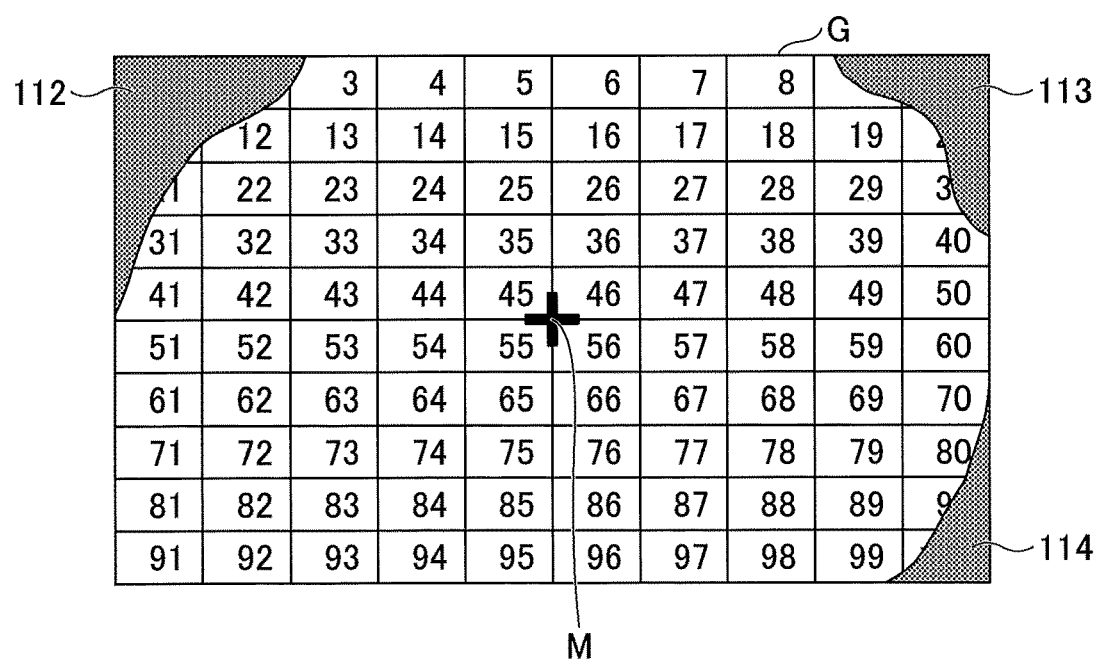
FIG. 21B is diagram illustrating an example of how the visual field examination image is visually perceived by the test subject P having the view as shown in FIG. 21A.

FIGS. 21A and 21B are a first set of diagrams illustrating an example of how a visual field examination image is visually perceived by a test subject. FIG. 21A is a diagram illustrating an example view (visual field) of a visual field examination image by the test subject P. FIG. 21B is a diagram illustrating an example manner in which the visual field examination image is visually perceived by the test subject P having the view as shown in FIG. 21A.

As shown in FIG. 21A, the visual field 111 of the test subject P includes defective areas 112, 113, and 114. These defective areas 112, 113, and 114 correspond to positions on the retina of the test subject P. That is, there is some type of abnormality in the retina of the test subject P at the positions corresponding to the defective areas 112, 113, and 114 of the visual field 111.

When the visual field examination image G is projected onto the retina of the test subject P having a visual field with defective areas as described above, the defective areas 112, 113, and 114 as shown in FIG. 21A will also be reflected in the visual field examination image G viewed by the test subject P.

As such, the visual field examination image G is visually perceived by the test subject P as an image as shown in FIG. 21B with missing portions (shaded portions) corresponding to the defective areas 112, 113, and 114. Thus, the numbers inscribed in the regions located at the positions corresponding to the defective areas cannot be visually perceived by the test subject P.

In the example of FIG. 21B, the regions with the identifiers "1", "2", "11", and "21" are included in the defective area 112, and the regions with the identifiers "9", "10", "20", and "30" are included in the defective area 113. Thus, these numbers correspond to numbers that cannot be read by the test subject P.

Figure 22:
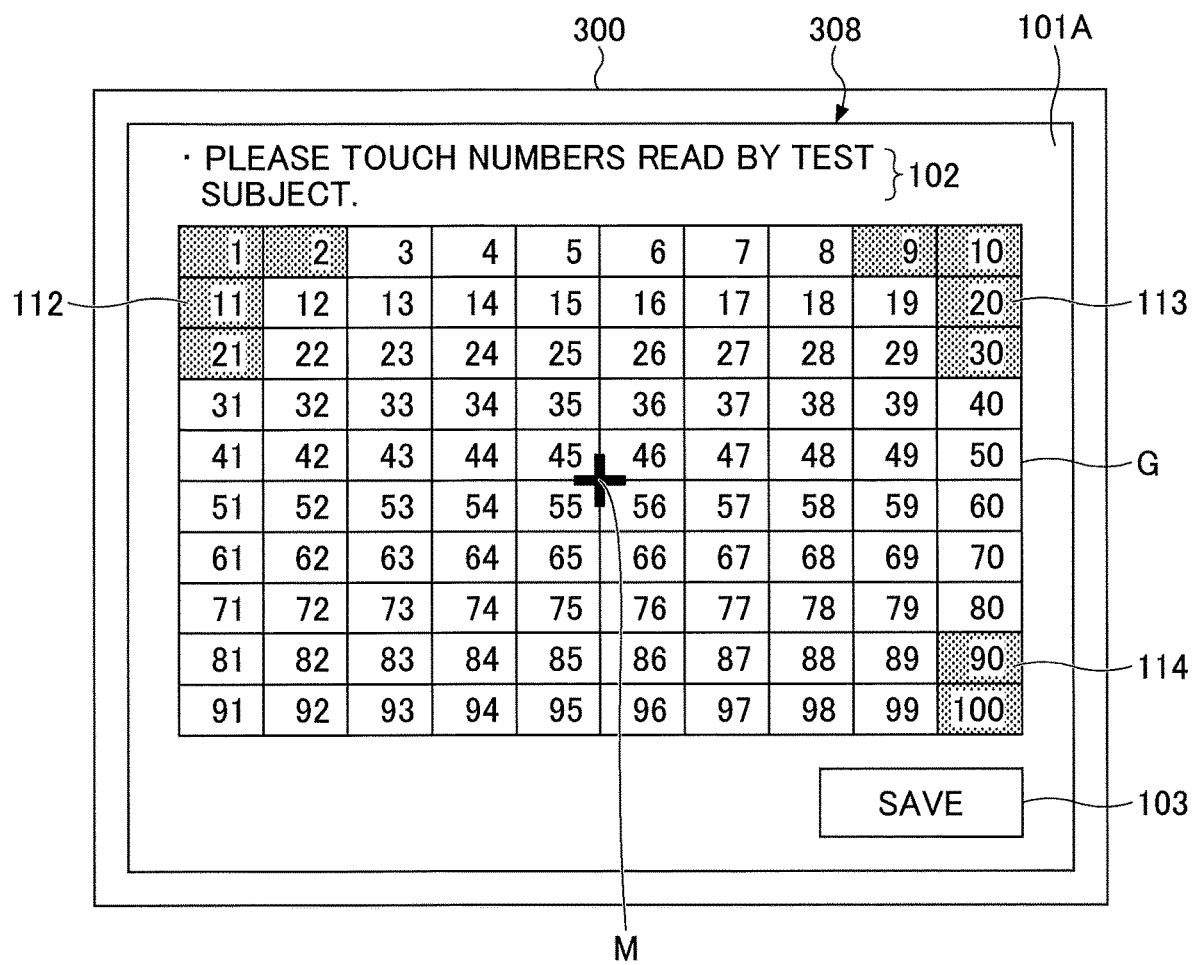
FIG. 22 is a first diagram illustrating an example of a visual field examination result input screen having a visual field examination result input thereto according to the first embodiment.

FIG. 22 is a first diagram showing an example of an examination result input screen having an examination result input thereto according to the first embodiment.

The examination result input screen 101A shown in FIG. 22 represents an example case where the examination result of the test subject P has been input to the examination result input screen 101.

In the examination result input screen 101A, the numbers in the regions included in the defective areas 112 to 114 are not selected, and the numbers in the regions other than the regions included in the defective areas 112 to 114 are selected.

Note that in the examination result input screen 101A of FIG. 22, the regions in the visual field examination image G that have been selected are displayed so that they appear brighter than the regions that have not been selected. However, the present invention is not limited thereto. The examination result input screen 101A is preferably configured to display the selected regions and the non-selected regions of the visual field examination image G in different modes so that they can be distinguished from each other.

It can be appreciated that in the examination result input screen 101A, the numbers 3-8, 12-19, 22-29, 31-89, and 91-99 were selected as numbers that could be read by the test subject P. Thus, it can be appreciated that out of the regions of the visual field examination image G displayed on the examination result input screen 101A, the regions inscribed with the numbers selected by the test subject P correspond to the visual field of the test subject P.

When input of the examination result to the examination result input screen 101A is completed and the button 103 is operated, the input examination result is stored in the visual field examination result table 331-P.

FIG. 23 is a first diagram showing an example of the visual field examination result table according to the first embodiment.

The visual field examination result table 331-P according to the present embodiment includes a test subject ID, an examination date, an input time, readable numbers, and unreadable numbers as items of information. In the visual field examination result table 331-P, the item "test subject ID" is associated with the other items of information. In the following description, information including the values of the items in the visual field examination result table 331-P is referred to as visual field examination result information.

The value of the item "test subject ID" is an identifier for identifying the test subject. Note that according to an aspect of the present embodiment, the name of the test subject or the like may be used as information identifying the test subject instead of an identifier, for example.

The value of the item "examination date" is information indicating the date on which the visual field examination was conducted. The value of the item "input time" is information indicating the time at which the examination result of the visual field examination was input to the terminal device 300. That is, the value of the item "input time" is information indicating the time at which the visual field examination was conducted.

The value of the item "readable numbers" indicates the numbers in the visual field examination image G that could be read by the user. In other words, the value of the item "readable numbers" indicates the numbers inscribed in the regions that were selected as having readable numbers from among the regions of the visual field examination image G displayed on the examination result input screen 101.

The value of the item "unreadable numbers" indicates the numbers in the visual field examination image G that could not be read by the user. In other words, the value of the item "unreadable numbers" indicates the numbers inscribed in the regions that were not selected as having readable numbers from among the regions of the visual field examination image G displayed on the examination result input screen 101.

As can be appreciated, the visual field examination result table 331-P shown in FIG. 23 stores examination results input by the test subject P with the test subject ID "001", including an examination result input at 10:00 on 2016 Apr. 10 and an examination result input at 18:00 on 2016 Apr. 13.

In the following, a visual field examination result table 331-Q for a test subject Q will be described with reference to FIGS. 24A to 26.

Figure 24A:
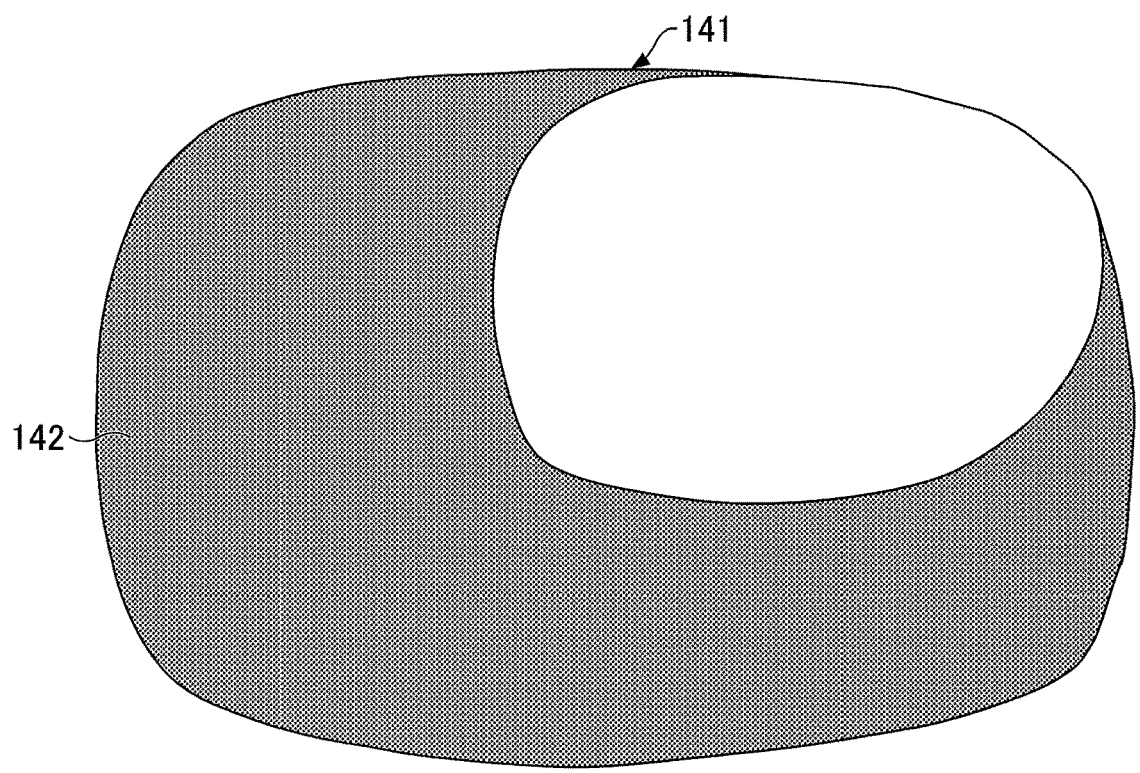
FIG. 24A is a diagram illustrating an example view of the visual field examination image as viewed by a test subject Q.
Figure 24B:
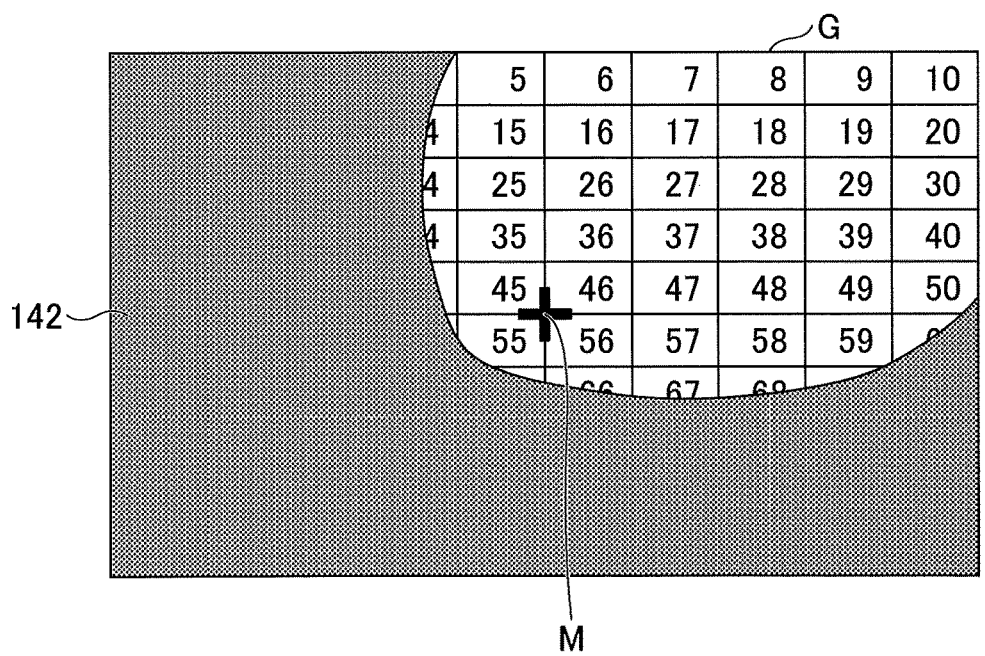
FIG. 24B is a diagram illustrating an example of how the visual field examination image is visually perceived by the test subject Q having the view as shown in FIG. 24A.

FIGS. 24A and 24B are a second set of diagrams illustrating an example of how a visual field examination image is visually perceived by a test subject. FIG. 24A shows an example view (visual field) of the test subject Q. FIG. 24B shows an example of how the visual field examination image G is visually perceived by the test subject Q having the view as shown in FIG. 24A.

As shown in FIG. 24A, the visual field 141 of the test subject Q includes a defective area 142.

Accordingly, the visual field examination image G is visually perceived by the test subject Q as an image having a missing portion at a position on the retina corresponding to the defective area 142 (shaded portion). As such, numbers inscribed in regions of the visual field examination image G located at the positions corresponding to the defective area 142 cannot be visually perceived by the test subject Q.

In the example of FIG. 24B, the numbers inscribed in the regions included in the defective area 142 correspond to numbers that cannot be read by the test subject Q.

Figure 25:
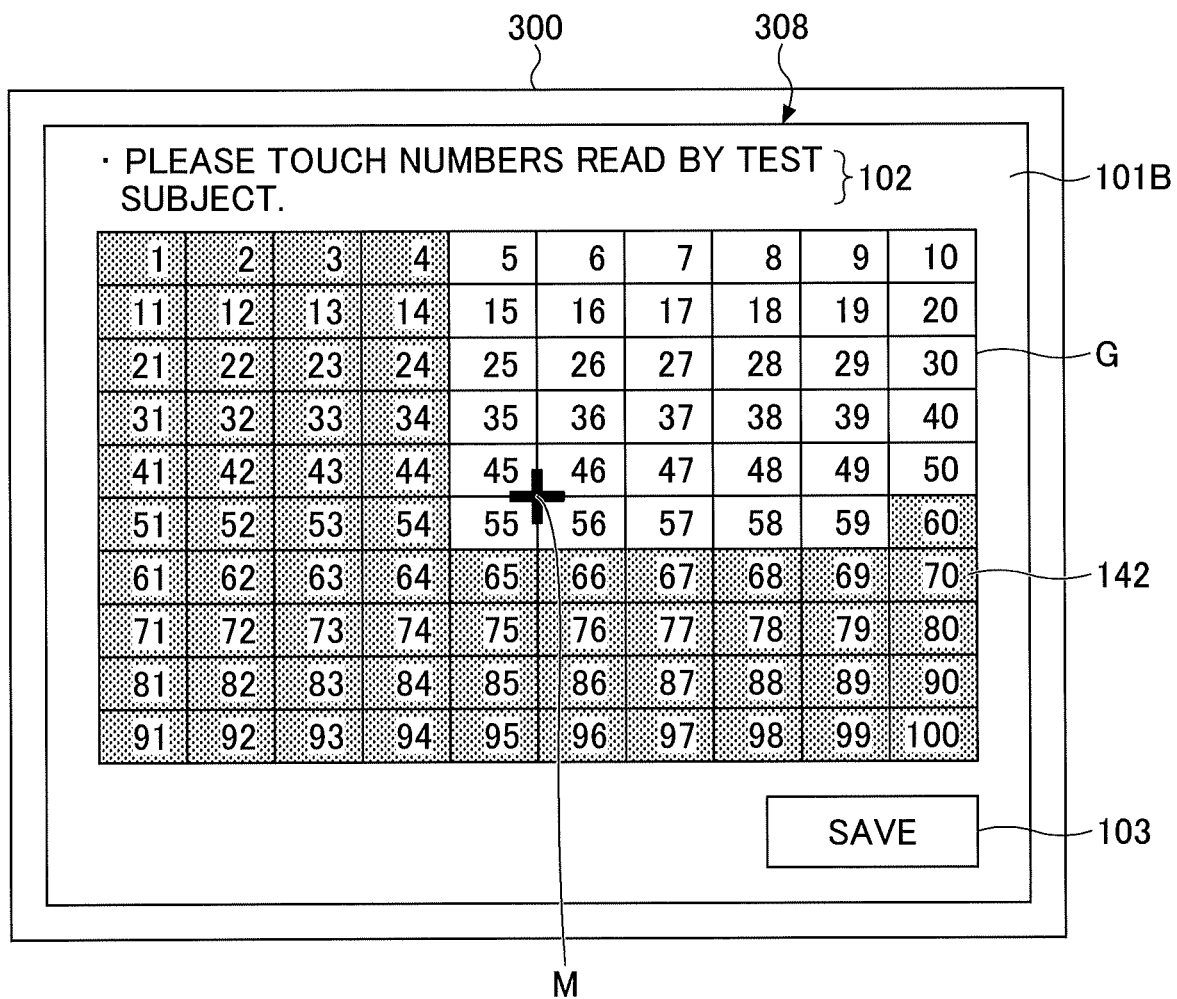
FIG. 25 is a second diagram illustrating an example of a visual field examination result input screen having a visual field examination result input thereto according to the first embodiment.

FIG. 25 is a second diagram showing an example of an examination result input screen having a visual field examination result input thereto according to the first embodiment.

The examination result input screen 101B shown in FIG. 25 represents an example case where an examination result of the test subject Q has been input to the examination result input screen 101.

It can be appreciated that in the examination result input screen 101B, the numbers inscribed in the regions included in the defective area 142 have not been selected, and the numbers inscribed in the regions other than the regions included in the defective area 142 have been selected.

It can be appreciated that in the examination result input screen 101B, the numbers 5-10, 15-20, 25-30, 35-40, 45-50, 55-59 have been selected as numbers that could be read by the test subject Q. Accordingly, it can be appreciated that the regions inscribed with the numbers selected by the test subject Q correspond to the visual field of the test subject Q.

When input of the examination result to the examination result input screen 101B is completed and the button 103 is operated, the input examination result is stored in a visual field examination result table 331-Q.

FIG. 26 is a second diagram showing an example of the visual field examination result table according to the first embodiment.

As can be appreciated, the visual field examination result table 331-Q shown in FIG. 26 stores examination results of visual field examinations conducted on the test subject Q with the test subject ID "002", including an examination result input at 10:00 on 2016 Apr. 10, and an examination result input at 18:00 on 2016 Apr. 13.

As described above, according to an aspect of the present embodiment, the Maxwellian view is used to directly project the visual field examination image G, which is divided into a plurality of regions, onto a predetermined position on the retina so that each region of the visual field examination image G corresponds to a position on the retina. Thus, by examining whether each region can be visually perceived, a visual field examination can be conducted with respect to each position on the retina corresponding to each region, for example.

According to an aspect of the present embodiment, the visual field examination result table 331 stored in the terminal device 300 may be stored in a server of a medical institution using the visual field/visual acuity examination system 100, for example.

Note that although the visual field examination image G has been described in the present embodiment as having a size covering the visual field of a test subject, the present invention is not limited thereto.

For example, according to an aspect of the present embodiment, the visual field/visual acuity examination device 200 may be provided with a mechanism for detecting the direction in which the pupil of a test subject has moved. By providing such a mechanism in the visual field/visual acuity examination device 200, the irradiation direction of image light beams from the light source 211 may be changed to be in the direction in which the pupil of the test subject has moved, for example.

In this way, the test subject can visually perceive the same visual field examination image G both before and after moving the pupil. Thus, the test subject does not have to face a fixed direction, and can undergo a visual field examination in any posture. Also, in this way, the test subject may be able to visually perceive the visual field examination image G at all times during the visual field examination irrespective of the posture of the test subject, for example, and the examination accuracy may be improved.

Also, in the visual field examination result table 331 according to an aspect of the present embodiment, for example, instead of including values of the item "readable numbers" and the item "unreadable numbers", coordinate information indicating the positions of the regions represented by the identifiers may be used. Further, the visual field examination result table 331 may include coordinate information indicating the positions of the regions represented by the values of the item "readable numbers" and the item "unreadable numbers" as items of information.

For example, the coordinate information may be acquired from the visual field examination image data, or may be acquired from a table associating the identifier of each region with coordinate information specifying the region corresponding to the identifier, for example. Such a table may be provided to the terminal device 300 in advance, for example.

Further, according to an aspect of the present embodiment, image data of the visual field examination image G having certain regions selected may be included in the visual field examination result information. That is, according to an aspect of the present embodiment, image data of the visual field examination image G having certain regions selected as shown in FIG. 12 or FIG. 15 may be stored as one item of information in the visual field examination result information.

Also, according to an aspect of the present embodiment, the brightness (luminance) of the visual field examination image G may be incrementally changed, and an examination result may be input each time a change is made, for example. In this case the visual field examination result table 331 may include an additional item "brightness of visual field examination image G", and the visual field examination result information may include the value of the item "brightness of visual field examination image G".

According to an aspect of the present embodiment, by inputting an examination result for each brightness level of the visual field examination image G, the visual field of the user for varying levels of brightness may be determined.

In the following, a visual acuity examination result table 332-Q for the test subject Q will be described with reference to FIGS. 27 to 29.

Figure 27:
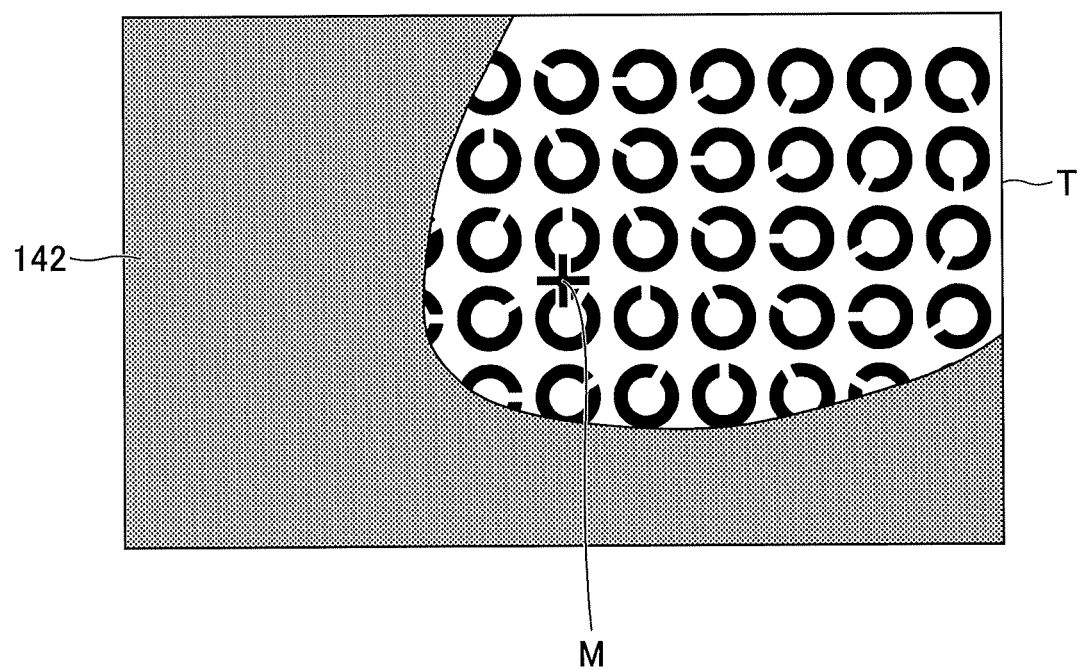
FIG. 27 is a diagram illustrating an example of how a visual acuity examination image is visually perceived by the test subject Q having the view as shown in FIG. 24A.

FIG. 27 is a diagram showing an example of how a visual acuity examination image is visually perceived by a test subject having a view as shown in FIG. 24A.

The visual field 141 of the test subject Q includes the defective area 142. As such, the visual acuity examination image T will be visually perceived by the test subject Q as an image as shown in FIG. 27 with a missing portion (shaded portion) corresponding to the defective area 142. That is, the Landolt rings drawn in the area located at the position corresponding to the defective area 142 cannot be visually perceived by the test subject Q. Thus, in the example of FIG. 27, the gaps of the Landolt rings drawn in the area corresponding to the defective area 142 cannot be discerned by the test subject Q.

FIG. 28 is a diagram showing an example of an examination result input screen having a visual acuity examination result input thereto according to the first embodiment.

The examination result input screen 101C shown in FIG. 28 represents an example case where a visual field examination result of the test subject Q has been input to an examination result input screen displaying the visual acuity examination image T.

In the present embodiment, visual acuity examination images T including Landolt rings of different sizes are sequentially projected onto the retina of the test subject Q. In the present embodiment, for example, the test subject Q may read out the directions of the gaps in the Landolt ring projected onto an area other than the defective area 142, and the examination assistant may operate the examination result input screen 101C to select the Landolt rings for which the test subject Q was able to discern the directions of the gaps.

Note that the examination assistant may not be able to easily determine that there is a defective area 142 in the visual field of the test subject Q or the location of the defective area 142 in the visual field of the test subject Q. Thus, for example, in the visual acuity examination image T, an identifier for identifying each Landolt ring may be provided at the center or in the vicinity of each Landolt ring.

For example, as shown in FIG. 28, each Landolt ring may be assigned a number as an identifier for identifying the Landolt ring and the number may be indicated at the center of each Landolt ring.

Also, it can be appreciated that in the examination result input screen 101C, the Landolt rings in the area corresponding to the defective area 142 are not selected, and the Landolt rings in the area other than the defective area 142 are selected.

It can be appreciated that in the examination result input screen 101C, the Landolt rings with the numbers 5-11, 16-22, 27-33, 38-44, and 50-52 have been selected as the Landolt rings for which the test subject Q was able to discern the gaps formed therein.

According to an aspect of the present embodiment, by conducting a visual acuity examination in the above-described manner, the visual acuity for the visual field of the test subject Q may be measured. Also, according to an aspect of the present embodiment, a visual field examination for determining whether a defective area exits in the visual field of the test subject Q may be conducted at the same time as a visual acuity examination.

When input of the visual acuity examination result to the examination result input screen 101C is completed and the button 103 is operated, the input visual acuity examination result is stored in the visual acuity examination result table 332-Q.

FIG. 29 is a first diagram showing an example of the visual acuity examination result table according to the first embodiment.

The visual acuity examination result table 332-Q according to the present embodiment includes a test subject ID, an examination date, an input time, indiscernible Landolt rings, and discernible Landolt rings as items of information. In the visual acuity examination result table 332-Q, the item "test subject ID" is associated with the other items of information. In the following description, information including the values of the items in the visual acuity examination result table 332-Q is referred to as visual acuity examination result information.

The value of the item "indiscernible Landolt rings" indicates the Landolt rings in the visual acuity examination image T for which the test subject Q was not able to discern the gaps formed therein. In other words, the value of the item "indiscernible Landolt rings" includes the identifiers identifying the Landolt rings that have not been selected as the Landolt rings that could be discerned by the test subject Q from among the Landolt rings in the visual acuity examination image T displayed on the examination result input screen 101C.

The value of the item "discernible Landolt rings" indicates the Landolt rings in the visual acuity examination image T for which the test subject Q was able to discern the gaps formed therein. In other words, the item "discernible Landolt rings" includes the identifiers identifying the Landolt rings selected as the Landolt ring that could be discerned by the test subject Q from among the Landolt rings in the visual acuity examination image T displayed on the examination result input screen 101C. It can be appreciated that the visual acuity examination result table 332-Q shown in FIG. 29 stores an examination result of a visual acuity examination conducted on the test subject Q with the test subject ID "002" that has been input at 10:00 on 2016 Apr. 10.

Note that in the example of FIG. 29, the values of the items "indiscernible Landolt rings" and "discernible Landolt rings" include identifiers identifying the Landolt rings, but the present invention is not limited thereto. For example, the values of the items "indiscernible Landolt rings" and "discernible Landolt rings" may include the coordinates of the center points of the Landolt rings selected via the examination result input screen 101C.

FIG. 30 is a second diagram showing an example of the visual acuity examination result table according to the first embodiment. The visual acuity examination result table 332A-Q shown in FIG. 30 shows an example of a visual acuity examination result when a moving image of one moving Landolt ring is projected onto the retina of the test subject Q.

In the visual acuity examination result table 332A-Q, the value of the item "discernible area" is information indicating the coordinates of an area in the visual acuity examination image T where the Landolt ring could be discerned by the test subject Q while the Landolt ring was being displayed.

Also, the value of the item "indiscernible area" is information indicating the coordinates of an area in the visual acuity examination image T where the Landolt ring could not be discerned by the test subject Q while the Landolt ring was being displayed. Note that the coordinates used herein may correspond to the coordinates of the center point of the Landolt ring, for example.

It can be appreciated that in the example of FIG. 30, the test subject Q was able to discern the gap in the Landolt ring when the center point of the Landolt ring was included in the range from coordinates (x3, y3) to coordinates (x4, y4). Similarly, it can be appreciated that in the example of FIG. 30, the test subject Q was unable to discern the gap in the Landolt ring when the center point of the Landolt ring was included in the range from coordinates (x1, y1) to coordinates (x2, y2).

Note that according to an aspect of the present embodiment, the expression "discerning the gap of the Landolt ring" may include both a case where a person visually perceives the Landolt ring and also correctly determines the direction of the gap in the Landolt ring, and a case where a person visually perceives the Landolt ring but does not correctly determine the direction of the gap in the Landolt ring.

As described above, according to an aspect of the present embodiment, the Maxwellian view is used to directly project the visual field examination image G, which is divided into a plurality of regions, onto a predetermined position of the retina so that each region of the visual field examination image G corresponds to a certain position on the retina. Thus, by examining whether each region can be visually perceived, a visual field examination can be conducted with respect to each position on the retinal corresponding to each region.

Also, according to an aspect of the present embodiment, the Maxwellian view is used to directly project the visual acuity examination image T, which includes one or more visual target images used for visual acuity examination, onto a predetermined position of the retina. In this way, in the present embodiment, the visual acuity of the retina itself can be measured. Further, in the present embodiment, the visual acuity distribution across the retina can be measured.

Second Embodiment

In the following, a second embodiment of the present invention will be described with reference to the drawings. The second embodiment differs from the first embodiment in that image data based on visual field examination result data is generated so that images and characters can be visually perceived even by a test subject having a visual field with a defect. In the following description of the second embodiment, only features that differ from those of the first embodiment are described, and features having the same functional configuration as those of the first embodiment are given the same reference numerals as those used in the description of the first embodiment and descriptions thereof will be omitted.

Figure 31:
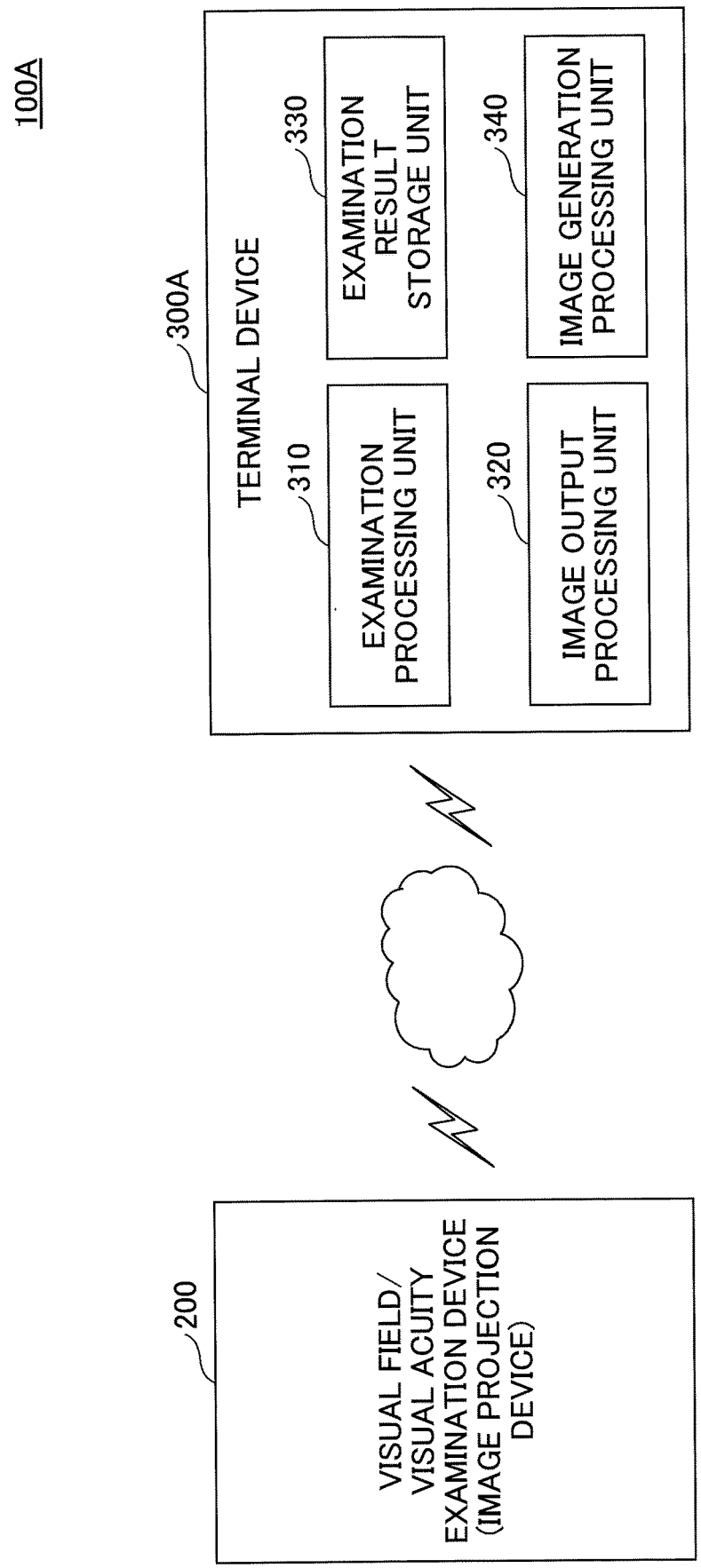
FIG. 31 is a diagram illustrating an example system configuration of a visual field/visual acuity examination system according to a second embodiment of the present invention.

FIG. 31 is a diagram illustrating an example system configuration of a visual field/visual acuity examination system according to the second embodiment.

The visual field/visual acuity examination system 100A according to the present embodiment includes a visual field/visual acuity examination device 200 and a terminal device 300A.

The visual field/visual acuity examination device 200 according to the present embodiment functions as an image projection device that projects not only examination image data for examination but also other various types of image data transmitted from the terminal device 300A onto the retina of a test subject.

The terminal device 300A according to the present embodiment includes an examination processing unit 310, an image output processing unit 320, an examination result storage unit 330, and an image generation processing unit 340.

The image generation processing unit 340 according to the present embodiment refers to the examination result stored in the examination result storage unit 330 to generate image data so that information to be projected (projection target) is projected onto the visual field of the test subject.

Figure 32:
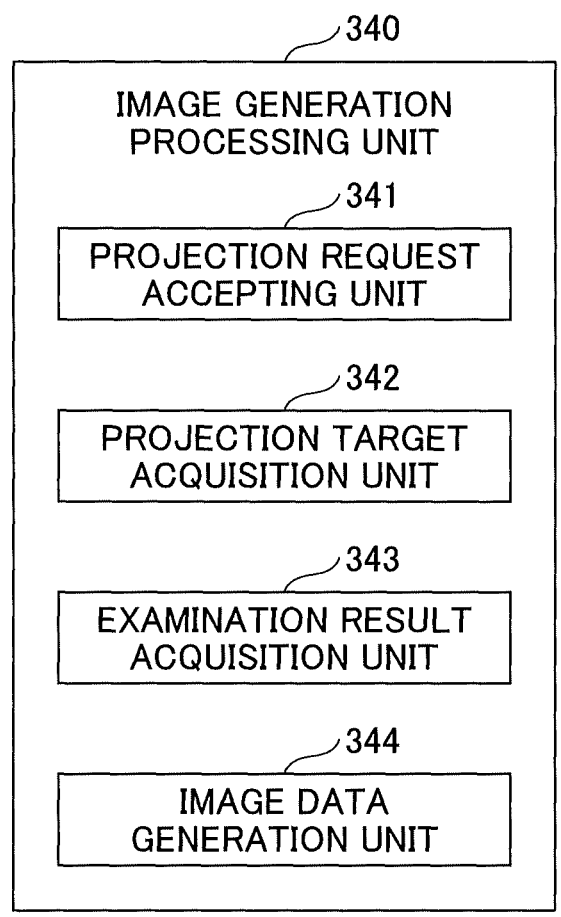
FIG. 32 is a diagram illustrating example functions of an image generation processing unit according to the second embodiment.

In the following, the image generation processing unit 340 according to the present embodiment will be described with reference to FIG. 32. FIG. 32 is a diagram illustrating example functions of the image generation processing unit according to the second embodiment.

The image generation processing unit 340 according to the present embodiment includes a projection request accepting unit 341, a projection target acquisition unit 342, an examination result acquisition unit 343, and an image data generation unit 344.

The projection request accepting unit 341 accepts a projection request for projecting projection information that has been input to the display operation device 301, for example.

The projection target acquisition unit 342 acquires projection information. Projection information refers to information that is to be the basis of an image to be projected onto the retina of the test subject P by the visual field/visual acuity examination device 200. For example, the projection information may be content data stored in the auxiliary storage device 303 of the terminal device 300A. Further, the projection information may be content data acquired by the terminal device 300A from an external server, a storage device, or the like. Also, the projection information may be text data or image data including a moving image, for example.

The examination result acquisition unit 343 acquires visual field examination result information with the most recent examination date and input time from the visual field examination result table 331 of the examination result storage unit 330.

The image data generation unit 344 refers to the visual field examination result information to generate image data of an image having projection information displayed in regions represented by the value of the item "readable numbers" and passes the generated image data to the image output processing unit 320.

Figure 33:
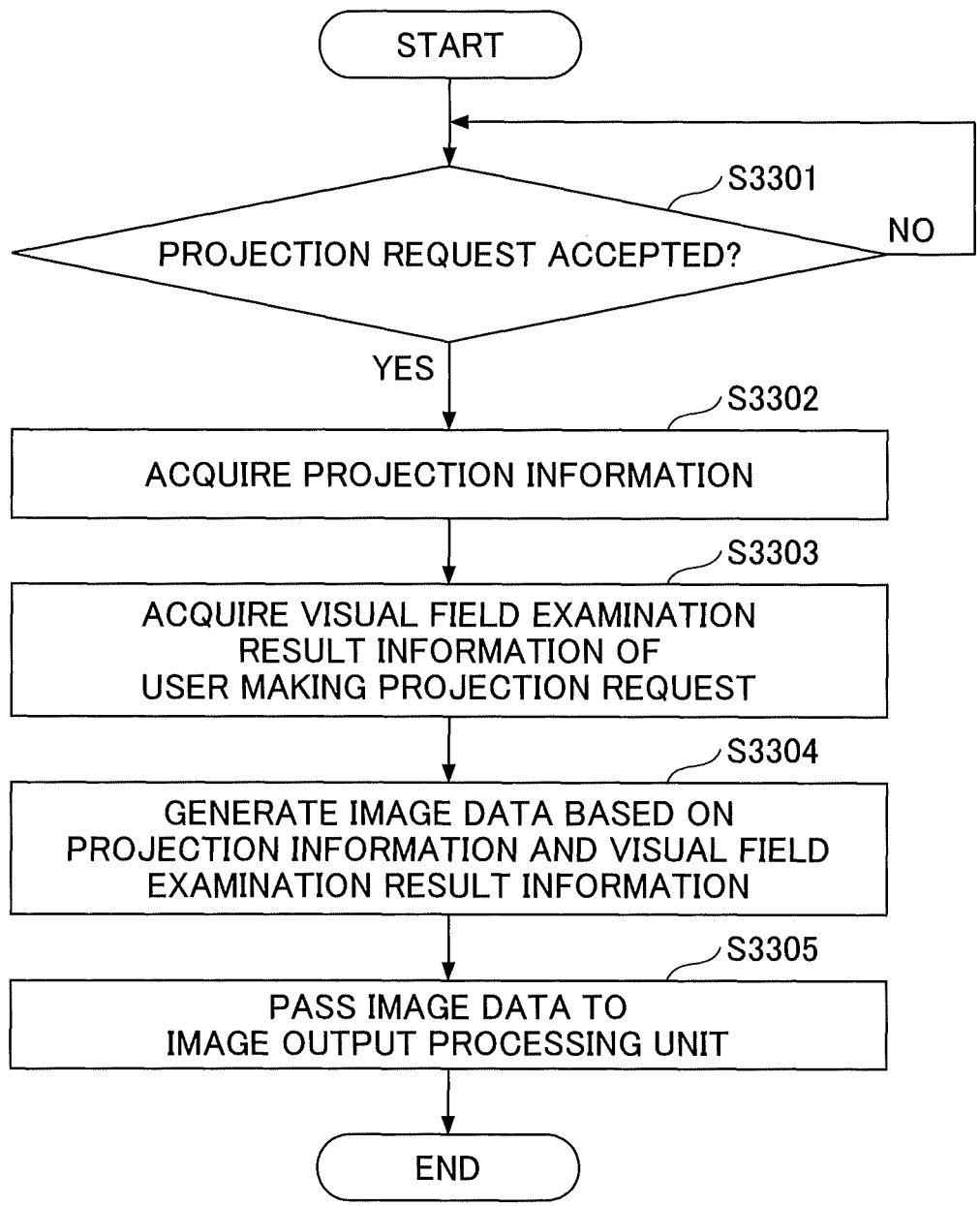
FIG. 33 is a flowchart illustrating example process operations of the image generation processing unit according to the second embodiment.

In the following, process operations of the image generation processing unit 340 according to the present embodiment will be described with reference to FIG. 33. FIG. 33 is a flowchart illustrating example process operations of the image generation processing unit according to the second embodiment.

In step S3301, the image generation processing unit 340 according to the present embodiment determines whether the projection request accepting unit 341 has accepted a selection of projection information and a projection request for projecting the projection information. Upon determining, in step S3301, that a projection request has not been accepted, the image generation processing unit 340 waits until a projection request is accepted.

Upon determining that a projection has been accepted in step S3301, the projection target acquisition unit 342 of the image generation processing unit 340 acquires the selected projection information (step S3302).

Then, the examination result acquisition unit 343 of the image generation processing unit 340 acquires the visual field examination result information of the test subject that has made the projection request from the visual field examination result table 331 of the examination result storage unit 330 (step S3304).

Then, the image data generation unit 344 of the image generation processing unit 340 generates image data to be passed to the image output processing unit 320 based on the examination result information (step S3305). Specifically, based on the examination result information, the image data generation unit 344 generates image data of an image having projection information displayed only in the regions corresponding to the item "readable numbers".

Then, the image data generation unit 344 passes the generated image data to the image output processing unit 320, and ends the process.

In the following, the image data generated by the image generation processing unit 340 according to the present embodiment will be described with reference to FIG. 34.

Figure 34:
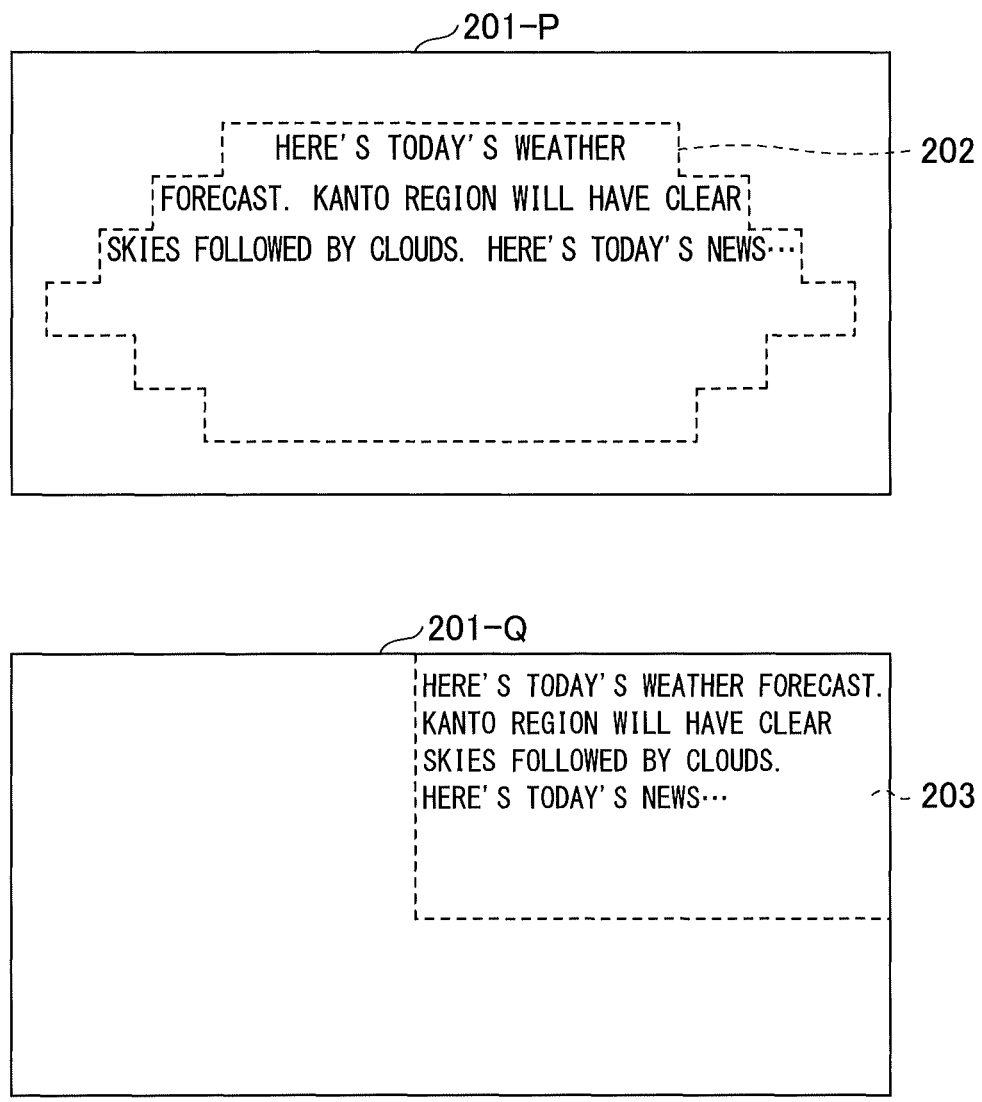
FIG. 34 is a diagram illustrating an example of image data generated by the image generation processing unit.

FIG. 34 is a diagram showing examples of image data generated by the image generation processing unit. In FIG. 34, an image 201-P is an example of an image represented by image data generated based on the examination result information of the test subject P, and an image 201-Q is an example of an image represented by image data generated based on the examination result information of the test subject Q.

In the visual field examination result table 331-P, the most recent examination result information is the examination result information input at 18:00 on 2016 Apr. 13 (see FIG. 23).

Thus, the image generation processing unit 340 acquires the visual field examination result information input at 18:00 on 2016 Apr. 13 from the visual field examination result table 331-P.

The value of the item "readable numbers" included in the visual field examination result information is 3-8, 12-19, 22-29, 31-89, and 91-98.

Thus, the image generation processing unit 340 generates image data representing the image 201-P having projection information displayed only in the regions having the above numbers as identifiers.

For example, the image 201-P has projection information displayed in the regions corresponding to the identifiers 12-19, the regions corresponding to the identifiers 22-29, the regions corresponding to the identifiers 31-89, and the like. In other words, the image 201-P has projection information displayed only in an area 202 corresponding to the visual field of the test subject P. Thus, according to an aspect of the present embodiment, projection information specified in a projection request made by the test subject P can be projected onto the retina of the test subject P in a manner such that the projection information is included in the visual field of the test subject P.

Also, in the visual field examination result table 331-Q, the most recent examination result information is the examination result information input at 18:00 on 2016 Apr. 13 (see FIG. 26).

Thus, the image generation processing unit 340 acquires the examination result information input at 18:00 on 2016 Apr. 13 from the visual field examination result table 331-Q.

The value of the item "readable numbers" included in the acquired examination result information is 5-10, 14-20, 24-30, 35-40, 44-50, and 55-60.

Thus, the image generation processing unit 340 generates image data representing the image 201-Q having the projection information displayed only in the regions having the above numbers as identifiers.

For example, the image 201-Q has the projection information displayed in regions corresponding to the identifiers 5-10, 14-20, 24-30, 35-40, 44-50, and 55-60. In other words, the image 201-Q has the projection information displayed only in an area 203 corresponding to the visual field of the test subject Q. Thus, according to an aspect of the present embodiment, projection information specified in a projection request made by the test subject Q can be projected onto the retina of the test subject Q in a manner such that the projection information is included in the visual field of the test subject Q.

As described above, according to an aspect of the present embodiment, a visual field examination result may be used to project an image only within the visual field of a test subject.

Thus, according to an aspect of the present embodiment, projection information may be projected onto the retina of a test subject without causing a partial loss of the projection information due to a defect in the visual field.

For example, according to an aspect of the present embodiment, when a person having a limited visual field searches for a term in an electronic dictionary or the like, only an image of a portion displaying the meaning of the term or the like may be extracted from the image displaying the search result of the searched term, and the extracted image may be displayed within the visual field of the person so that even a person having a limited visual field may be able to use a normal electronic dictionary.

Also, clinical results have revealed that even a person having a limited visual field can "read" if, in the case of Japanese, at least five characters can be placed in the visual field of the person. Note that the term "reading" as used herein means following characters with the eyes and understanding the meaning thereof (see Osaka, N. & Oda, K. (1991). Effective visual field size necessary for vertical reading during Japanese text processing. Bulletin of the Psychonomic Society, 29(4), 345-347.).

Thus, according to an aspect of the present embodiment, for example, even a person having a visual field with a large defective area and difficulty reading may be able to read text by having at least five characters projected within the visual field of the person.

Note that image data generated by the image generation processing unit 340 according to the present embodiment may also include moving image data. For example, in the case of projecting the content of an electronic book onto the visual field of a person, moving image data may be projected so that text data moves across the visual field of the person.

Further, the image generation processing unit 340 according to the present embodiment may refer to the visual acuity examination result information of test subject using the visual field/visual acuity examination device 200, and when the value of the item "discernible Landolt rings" includes values indicating a plurality of Landolt rings, the image generation processing unit 340 may adjust the size of characters to be projected according to the size of these Landolt rings.

In this way, characters in a size according to the visual acuity of the retina itself may be projected onto the visual field.

Also, in the image generation processing unit 340 according to the present embodiment, the image data generation unit 344 generates image data of an image projecting information only within the visual field of the test subject. However, the present invention is not limited thereto.

For example, the image generation processing unit 340 may transmit information indicating the visual field of the test subject and image data for projecting only the projection information to the visual field/visual acuity examination device (image projection device) 200 via the image output processing unit 320. The information indicating the visual field of the test subject may be coordinate information of regions having the values of the item "readable numbers" included in the examination result information of the test subject as identifiers, for example.

When the visual field/visual acuity examination device (image projection device) 200 receives the input of information indicating the visual field of the test subject and image data for projecting only the projection information, the control unit 230 may control the vibration of the scanning mirror 212 so that the projection information will only be projected within the visual field of the test subject.

Third Embodiment

In the following, a third embodiment of the present invention will be described with reference to the drawings. The third embodiment differs from the second embodiment in that the functions of the terminal device according to the second embodiment are provided in an external server outside the terminal device. In the following description of the third embodiment, features having substantially the same functional configuration as those of the second embodiment are given the same reference numerals as those used in the description of the second embodiment, and descriptions thereof will be omitted.

Figure 35:
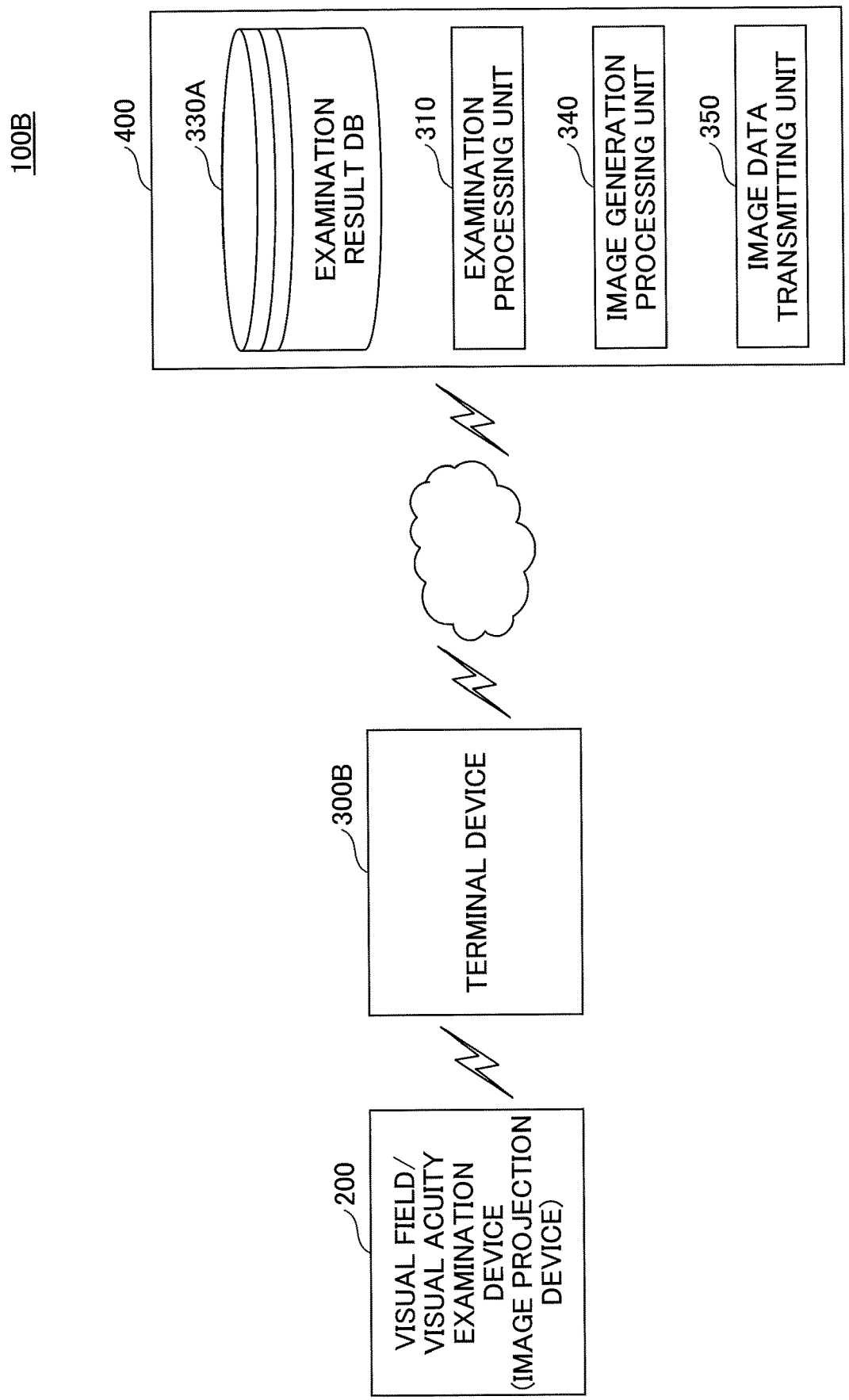
FIG. 35 is a diagram illustrating an example system configuration of a visual field/visual acuity examination system according to a third embodiment of the present invention.

FIG. 35 is a diagram illustrating an example system configuration of the visual field/visual acuity examination system according to the third embodiment.

The visual field/visual acuity examination system 100B according to the present embodiment includes a visual field/visual acuity examination device (image projection device) 200, a terminal device 300B, and a server 400. Note that although one visual field/visual acuity examination device (image projection device) 200 and one terminal device 300B are illustrated in FIG. 35, the number of the visual field/visual acuity examination devices (image projection device) 200 and the number of terminal devices 300B included in the visual field/visual acuity examination system 100B may be any number.

The terminal device 300B according to the present embodiment receives image data from the server 400 and transmits the received image data to the visual field/visual acuity examination device (image projection device) 200. Also, the terminal device 300B according to the present embodiment displays a screen specified by the server 400 and transmits information that has been input to the screen to the server 400.

The server 400 according to the present embodiment is connected to the terminal device 300B via a network. The server 400 includes an examination result database 330A, an examination processing unit 310A, an image output processing unit 320, and an image generation processing unit 340.

The examination result database 330A according to the present embodiment stores visual field examination result information and visual acuity examination result information that have been input to the terminal device 300B in association with the test subject ID and information indicating the date/time the examination result information was input. Specifically, for example, in the case where a plurality of terminal devices 300B are provided, the examination result database 330A stores visual field examination result information and visual acuity examination result information input at the plurality of terminal devices 300B for each test subject ID.

In the examination processing unit 310A according to the present embodiment, the display control unit 312 causes the terminal device 300B to display an examination result input screen including examination image data. Further, in the examination processing unit 310A according to the present embodiment, the input accepting unit 313 accepts information input to the examination result input screen displayed by the terminal device 300B.

The image generation processing unit 340 according to the present embodiment outputs examination image data and image data generated by the image generation processing unit 340 to the terminal device 300B. The terminal device 300B transmits the examination image data and the image data generated by the image generation processing unit 340 to the visual field/visual acuity examination device 200.

As described above, in the present embodiment, the examination processing unit 310A and the image generation processing unit 340 are provided in the server 400, and in this way the processing load of the terminal device 300B can be reduced.

Fourth Embodiment

In the following, a fourth embodiment of the present invention will be described with reference to the drawings. The fourth embodiment differs from the second embodiment in that a server delivers an application including the functions of the examination processing unit, the image generation processing unit, and the image output processing unit to the terminal device. In the following description of the fourth embodiment, features that have substantially the same functional configuration as those of the second embodiment are given the same reference numerals as those used in the description of the second embodiment and descriptions thereof will be omitted.

FIG. 36 is a diagram illustrating an example system configuration of a visual field/visual acuity examination system according to the fourth embodiment.

The visual field/visual acuity examination system 100C according to the present embodiment includes a visual field/visual acuity examination device (image projection device) 200, a terminal device 300B, and a server 400A.

The server 400A according to the present embodiment includes an application delivering unit 410. Further, the server 400A includes an application 420 for implementing the functions of the examination processing unit 310, the image output processing unit 320, and the image generation processing unit 340.

In the server 400A according to the present embodiment, upon receiving a delivery request for the application 420 from the terminal device 300C, the application delivering unit 410 delivers the application 420 to the terminal device 300C that has issued the delivery request.

The terminal device 300C that has received the application 420 delivered from the server 400A becomes the terminal device 300A including the examination processing unit 310, the image output processing unit 320, and the image generation processing unit 340. Thus, in the present embodiment, the terminal device 300C that has received the application 420 delivered from the server 400A is capable of implementing the functions of the terminal device according to the second embodiment on its own, such as performing a visual field examination, generating image data based on the examination result, and providing the generated image data to the visual field/visual acuity examination device 200.

Although the present invention has been described with reference to illustrative embodiments, the present invention is not limited to the above embodiments, and numerous variations and modifications may be made without departing from the scope of the present invention.

The present application is based on and claims the benefit of priority of Japanese Patent Application No. 2016-115045 filed on Jun. 9, 2016, and Japanese Patent Application No. 2017-106337 filed on May 30, 2017, the entire contents of which are herein incorporated by reference.

DESCRIPTION OF THE REFERENCE NUMERALS 100, 100A, 100B visual field/visual acuity examination system
200 visual field/visual acuity examination device
300, 300A, 300B, 300C, 300D terminal device
310 examination processing unit
311 image data holding unit
312 display control unit
314 examination result storage control unit
320 image output processing unit
330 examination result storage unit
331 visual field examination result table
332 visual acuity examination result table
330A examination result database
340 image generation processing unit
342 projection target acquisition unit
343 examination result acquisition unit
344 image data generation unit
400 server
410 application distribution unit

The invention claimed is:

1. A visual field/visual acuity examination system comprising:
a retinal projection head-mounted display; and
a terminal device that communicates with the retinal projection head-mounted display;
wherein the terminal device includes
a memory;
a display; and
a processor configured to
hold examination image data including visual acuity examination image data, and visual field examination image data that is divided into a plurality of regions where each of the plurality of regions includes character or image data as an identifier;
store examination result data that indicates, among the plurality of regions, regions whose identifiers can be visually recognized by a test subject, and regions whose identifiers cannot be visually recognized by the test subject, in the memory;
generate, based on the examination result data, image data of projection information to be projected on a retina of an eyeball of the test subject in the regions whose identifiers can be visually recognized by the test subject;
output the examination image data and the image data of the projection information to the retinal projection head-mounted display;
display an image on the display; and
generate an examination image based on the examination image data and display the examination image on the display;
wherein the retinal projection head-mounted display includes
a light source configured to emit a light beam;
a scanning mirror;
a memory; and
a processor configured to
input the examination image data from the terminal device;
control emission of an image light beam based on the input examination image data and the image data of the projection information;
cause the scanning mirror to scan the image light beam; and
project the image light beam on the retina of the eyeball of the test subject.

2. The visual field/visual acuity examination system according to claim 1, wherein
the processor of the terminal device is further configured to select either the visual field examination image data or the visual acuity examination image data according to a selected examination type; and
output the visual field examination image data or the visual acuity examination image data that has been selected to the retinal projection head-mounted display.

3. The visual field/visual acuity examination system according to claim 2, wherein
the selected region corresponds to a region of the visual field examination image including an identifier that was visually perceived by the test subject or a region of the visual field examination image including an identifier that was not visually perceived by the test subject.

4. The visual field/visual acuity examination system according to claim 3, wherein
the processor of the terminal device displays on the display the visual field examination image along with a message prompting selection of the region of the visual field examination image including the identifier that was visually perceived by the test subject.

5. The visual field/visual acuity examination system according to claim 4, wherein
the identifiers are Arabic numerals; and
the examination image includes an image having the Arabic numerals inscribed in the plurality of regions.

6. The visual field/visual acuity examination system according to claim 5, wherein
the processor of the terminal device is further configured to store visual acuity examination result information in the memory, the visual acuity examination result information including information specifying a visual target image of a visual target selected from a visual acuity examination image based on the visual acuity examination image data that has been displayed on the display.

7. The visual field/visual acuity examination system according to claim 6, wherein
the visual target is a Landolt ring, and the information specifying the visual target image includes coordinates of a center point of the Landolt ring.

8. The visual field/visual acuity examination system according to claim 6, wherein
the processor of the terminal device outputs a plurality of sets of the visual acuity examination image data including the visual target images in different sizes to the retinal projection head-mounted display.

9. The visual field/visual acuity examination system according to claim 6, wherein
a size of an image of a character that is included in the image data of the image to be projected onto the retina of the test subject is determined based on the visual acuity examination result information stored in the memory.

10. The visual field/visual acuity examination system according to claim 1, wherein the visual acuity examination image data includes a visual target image of a visual target.

11. A retinal projection head-mounted display comprising:
a light source configured to emit a light beam;
a scanning mirror;
a memory; and
a processor configured to
input examination image data;
control emission of an image light beam based on the input examination image data and image data of projection information;
cause the scanning mirror to scan the image light beam; and
project the image light beam on a retina of an eyeball of a test subject;
hold the examination image data including visual acuity examination image data, and visual field examination image data that is divided into a plurality of regions where each of the plurality of regions includes character or image data as an identifier;
store examination result data that indicates, among the plurality of regions, regions whose identifiers can be visually recognized by the test subject, and regions whose identifiers cannot be visually recognized by the test subject, in the memory; and
generate, based on the examination result data, image data of projection information to be projected on the retina of the eyeball of the test subject in the regions whose identifiers can be visually recognized by the test subject.

12. A visual field/visual acuity examination method to be implemented by a visual field/visual acuity examination system including
a retinal projection head-mounted display that includes a light source configured to emit a light beam, a scanning mirror, a memory, and a processor, and
a terminal device that communicates with the retinal projection head-mounted display, and includes a memory, a display, and a processor,
the visual field examination method comprising steps of:
the terminal device holding examination image data including visual acuity examination image data, and visual field examination image data that is divided into a plurality of regions where each of the plurality of regions includes character or image data as an identifier, in the memory;
the terminal device storing examination result data that indicates, among the plurality of regions, regions whose identifiers can be visually recognized by a test subject, and regions whose identifiers cannot be visually recognized by the test subject, in the memory;
the terminal device generating, based on the examination result data, image data of projection information to be projected on a retina of an eyeball of the test subject in the regions whose identifiers can be visually recognized by the test subject;
the terminal device outputting the examination image data and the image data of the projection information to the retinal projection head-mounted display;
the terminal device generating an examination image based on the examination image data and displaying the generated examination image on the display;
the retinal projection head-mounted display inputting the examination image data from the terminal device;
the retinal projection head-mounted display controlling emission of an image light beam based on the input examination image data and the image data of the projection information;
the retinal projection head-mounted display scanning the image light beam with a scanning mirror; and
the retinal projection head-mounted display projecting the examination image light beam on the retina of the eyeball of the test subject.

13. A visual field/visual acuity examination system comprising:
a visual field/visual acuity examination device; and
a terminal device that communicates with the visual field/visual acuity examination device;
wherein the terminal device includes
a memory;
a display; and
a processor configured to
hold examination image data including visual acuity examination image data, and visual field examination image data that is divided into a plurality of regions where each of the plurality of regions includes character or image data as an identifier;
store examination result data that indicates, among the plurality of regions, regions whose identifiers can be visually recognized by a test subject, and regions whose identifiers cannot be visually recognized by the test subject, in the memory;

generate, based on the examination result data, image data of projection information to be projected on a retina of an eyeball of the test subject in the regions whose identifiers can be visually recognized by the test subject;

output the examination image data and the image data of the projection information to a retinal projection head-mounted display;

display an image on the display; and generate an examination image based on the examination image data and display the examination image on the display;

wherein the visual field/visual acuity examination device includes a light source configured to emit a light beam;

a scanning mirror;

a memory; and a processor configured to input the examination image data from the terminal device;

control emission of an image light beam based on the input examination image data and the image data of the projection information;

cause the scanning mirror to scan the image light beam; and project the image light beam on the retina of the eyeball of the test subject.

14. A visual field/visual acuity examination device comprising:

a light source configured to emit a light beam;

a scanning mirror;

a memory; and a processor configured to input examination image data and data of projection information;

control emission of an image light beam based on the input examination image data and the image data of the projection information;

cause the scanning mirror to scan the image light beam; and project the image light beam on a retina of an eyeball of a test subject;

hold examination image data including visual acuity examination image data, and visual field examination image data that is divided into a plurality of regions where each of the plurality of regions includes character or image data as an identifier;

store examination result data that indicates, among the plurality of regions, regions whose identifiers can be visually recognized by the test subject, and regions whose identifiers cannot be visually recognized by the test subject, in the memory; and generate, based on the examination result data, the image data of the projection information to be projected on the retina of the eyeball of the test subject in the regions whose identifiers can be visually recognized by the test subject.

* * * * *